US010919983B2

(12) United States Patent
Bebbington et al.

(10) Patent No.: US 10,919,983 B2
(45) Date of Patent: Feb. 16, 2021

(54) IMMUNOGLOBULIN VARIABLE REGION CASSETTE EXCHANGE

(71) Applicant: HUMANIGEN, INC., Burlingame, CA (US)

(72) Inventors: Christopher Robert Bebbington, San Mateo, CA (US); Kenneth R. Luehrsen, Santa Barbara, CA (US); Geoffrey T. Yarranton, Burlingame, CA (US)

(73) Assignee: HUMANIGEN, INC., Burlingame, CA (US)

( * ) Notice: Subject to any disclaimer, the term of this patent is extended or adjusted under 35 U.S.C. 154(b) by 178 days.

(21) Appl. No.: 14/968,709

(22) Filed: Dec. 14, 2015

(65) Prior Publication Data

US 2016/0102152 A1  Apr. 14, 2016

Related U.S. Application Data

(63) Continuation of application No. 11/282,107, filed on Nov. 16, 2005, now abandoned.

(60) Provisional application No. 60/628,581, filed on Nov. 16, 2004.

(51) Int. Cl.
| | | |
|---|---|---|
| *C07K 16/46* | (2006.01) | |
| *C07K 16/00* | (2006.01) | |
| *C07K 1/107* | (2006.01) | |

(52) U.S. Cl.
CPC .......... *C07K 16/464* (2013.01); *C07K 1/1075* (2013.01); *C07K 16/005* (2013.01); *C07K 2317/21* (2013.01); *C07K 2317/24* (2013.01); *C07K 2317/55* (2013.01); *C07K 2317/56* (2013.01); *C07K 2317/565* (2013.01); *C07K 2317/567* (2013.01)

(58) Field of Classification Search
None
See application file for complete search history.

(56) References Cited

U.S. PATENT DOCUMENTS

| | | | |
|---|---|---|---|
| 5,225,539 A | 7/1993 | Winter | |
| 5,565,332 A | 10/1996 | Hoogenboom et al. | |
| 5,585,089 A | 12/1996 | Queen et al. | |
| 5,693,761 A | 12/1997 | Queen et al. | |
| 5,693,762 A | 12/1997 | Queen et al. | |
| 5,837,242 A | 11/1998 | Holliger et al. | |
| 5,859,205 A | 1/1999 | Adair et al. | |
| 6,180,370 B1 | 1/2001 | Queen et al. | |
| 6,248,516 B1 | 6/2001 | Winter et al. | |
| 6,350,861 B1 | 2/2002 | Co et al. | |
| 6,548,640 B1 | 4/2003 | Winter | |
| 6,969,586 B1 | 11/2005 | Lerner et al. | |
| 7,087,409 B2 | 8/2006 | Barbas et al. | |
| 7,981,843 B2 | 7/2011 | Flynn et al. | |
| 2003/0166871 A1 | 9/2003 | Barbas et al. | |
| 2003/0219839 A1 | 11/2003 | Bowdish et al. | |
| 2003/0235582 A1 | 12/2003 | Singh et al. | |
| 2005/0008625 A1 | 1/2005 | Balint et al. | |
| 2005/0169915 A1 | 8/2005 | Do Couto et al. | |
| 2005/0255552 A1 | 11/2005 | Flynn et al. | |
| 2007/0183970 A1 | 8/2007 | Goldenberg et al. | |
| 2009/0175847 A1 | 7/2009 | Barghorn et al. | |

FOREIGN PATENT DOCUMENTS

| | | |
|---|---|---|
| CA | 2082160 | 9/1992 |
| WO | WO 97/08320 | 3/1997 |
| WO | WO 02/00005 | 1/2002 |
| WO | WO-03/070760 | 8/2003 |
| WO | WO 2003/070760 | 8/2003 |
| WO | WO 2003/099999 | 12/2003 |
| WO | WO 2004/006955 | 1/2004 |
| WO | WO-2004/006955 | 1/2004 |
| WO | WO 2006/055178 | 5/2006 |

OTHER PUBLICATIONS

Al-Lazikani, B., "Standard conformations for the canonical structures of immunoglobulins," J. Mol. Biol., vol. 273, pp. 927-948 (1997).
Bajorath, J., et al., "Conformational similarity and systematic displacement of complementarity determining region loops in high resolution antibody x-ray structures," J. Bio. Chem., vol. 270(38), pp. 22081-22084 (1995).
Beiboer, S.H. et al., "Guided selection of a pan carcinoma specific antibody reveals similar binding characteristics yet structural divergence between the original murine antibody and its human equivalent," 2000, J. Mol. Biol., vol. 296(3), pp. 833-849.
Casset et al., Biochemical and Biophysical Research Communications, 307:198-205, 2003.
Chung, J. et al., "Integrin αIIbβ3 specific synthetic human monoclonal antibodies and HCDR3 peptides that potently inhibit platelet aggregation," Epub Dec. 19, 2003, FASEB J, 23 pages. (Final version cited as: 2004, vol. 18(2), pp. 361-363).
Colman, P.M., Research in Immunology, 145:33-36, 1994.
Daugherty, P.S. et al., "Development of an optimized expression system for the screening of antibody libraries displayed on the *Escherichia coli* surface," 1999, Protein Engineering, vol. 12(7), pp. 613-621.
Feldhaus, M.J. et al., "Flow-cytometric isolation of human antibodies from a nonimmune *Saccharomyces cerevisiae* surface display library," 2003, Nature Biotechnology, vol. 21 (2), pp. 163-170.
Fundamental Immunology, 3rd Edition, William E. Paul M.D., ed., pp. 292-295, 1993.

(Continued)

*Primary Examiner* — Brad Duffy
(74) *Attorney, Agent, or Firm* — Mark S. Cohen; Pearl Cohen Zedek; Latzer Baratz LLP

(57) ABSTRACT

The invention provides methods for generating human antibodies with the specificity of a reference antibody by replacement of portions of the $V_H$ and $V_L$ sequences of the reference antibody with sequences from human antibody repertoires. The invention also provides novel compositions comprising hybrid immunoglobulin variable domains containing a combination of frameworks (FRs) and CDRs from different antibody clones.

19 Claims, 7 Drawing Sheets

Specification includes a Sequence Listing.

(56) References Cited

OTHER PUBLICATIONS

Hoogenboom, H.R. and G. Winter, "By-passing immunisation. Human antibodies from synthetic repertoires of germline VH gene segments rearranged in vitro," 1992, J. Mol. Biol., vol. 227(2), pp. 381-388.

Jespers, L. et al., "Guiding the selection of human antibodies from phage display repertoires to a single epitope of an antigen," 1994, Bio/technology, vol. 12(9), pp. 899-903.

Jirholt, P. et al., "Exploiting sequence space: shuffling in vivo formed complementarity determining regions into a master framework," 1998, Gene, vol. 215(2), pp. 471-476.

P.T. et al., "Replacing the complementarity-determining regions in a human antibody with those from a mouse," 1986, Nature, vol. 321(29), pp. 522-525.

Kettleborough et al., "Humanization of a mouse monoclonal antibody by CDR-grafting: the importance of framework residues on loop conformation," Protein Eng., 4(7), pp. 773-783, 1991.

Klimka, A. et al., " Human anti-CD30 recombinant antibodies by guided phage antibody selection using cell panning," 2000, Br. J. Cancer, vol. 83(2), pp. 252-260.

Knappik et al., "Fully Synthetic Human Combinatorial Antibody Libraries (HuCAL) Based on Modular Consensus Frameworks and CDRs Randomized with Trinucleotides", J. Mol. Biol., 296:57-86, 2000.

MacCallum et al., J. Mol. Biol., 262, 732-745, 1996.

Mariuzza et al. (Annu. Ref. Biophys. Biophys.Chem. 1987; 16:139-159).

Marks, J.D. et al., "By-passing immunization: Human antibodies from V-gene libraries displayed on phage," 1991, J. Mol. Biol., vol. 222(3), pp. 581-597.

Marks, J.D. et al., "By-passing immunization: Building high affinity human antibodies by chain shuffling," 1992, Nature Biotechnology, vol. 10, pp. 779-783.

Martin, A.C.R. et al., "Molecular modeling of antibody combining sites," 1991, Methods in Enzymology, vol. 203, pp. 121-153.

Proba, K. et al., "Antibodies scFv fragments without disulfide bonds made by molecular evolution," J. Mol. Biol., vol. 275, pp. 245-253 (1998).

Queen, C. et al., "A humanized antibody that binds to the interleukin 2 receptor," 1989, PNAS, vol. 86(24), pp. 10029-10033.

Rader, C. et al., "A phage display approach for rapid antibody humanization: Designed combinatorial V gene libraries," 1998, PNAS, vol. 95(15), pp. 8910-8915.

Rader, C. et al., "The rabbit antibody repertoire as a novel source for the generation of therapeutic human antibodies," 2000, J. Biol. Chem., vol. 275(18), pp. 13668-13676.

Riechmann, L. et al., "Reshaping human antibodies for therapy," 1988, Nature, vol. 332, pp. 323-327.

Rudikoff et al., "Single amino acid substitution altering antigen-binding specificity", PNAS, 79, pp. 1979-1983, Mar. 1982.

Soderlind, E. et al., "Recombining germline-derived CDR sequences for creating diverse single-framework antibody libraries," 2000, Nature Biotechnology, vol. 18(8), pp. 852-856.

Steinberger, P. et al., "Generation and characterization of a recombinant human CCR5-specific antibody. A phage display approach for rabbit antibody humanization," 2000, J. Biol. Chem., vol. 275(46), pp. 36073-36078.

Verhoeyen, M. et al., "Reshaping human antibodies: grafting an antilysozyme activity," 1988, Science, vol. 239, pp. 1534-1536.

Winter, G. et al., "Making antibodies by phage display technology," 1994, Annu. Rev. Immunol., vol. 12, pp. 433-455.

International Search Report and Written Opinion, dated Sep. 21, 2006, from International Application No. PCT/US05/41825.

Extended European Search Report, dated Feb. 20, 2008, from European Application No. 05851809.3.

Extended European Search Report, dated May 24, 2011, from European Application No. 10014128.2.

Office Action, dated Jun. 18, 2012, from Canadian Application No. 2,587,158.

Office Action, dated Apr. 12, 2013, from Canadian Application No. 2,587,158.

Office Action, dated Dec. 20, 2013, from Canadian Application No. 2,587,158.

Office Action, dated Jan. 31, 2011, from European Application No. 05 851 809.3.

Office Action, dated Feb. 1, 2012, from European Application No. 05 851 809.3.

Office Action, dated Jul. 4, 2012, from European Application No. 05 851 809.3.

Office Action, dated Jun. 11, 2012, from European Application No. 10 014 128.2.

Office Action, dated Oct. 19, 2015, from European Application No. 10 014 128.2.

Office Action, dated Dec. 5, 2016, from European Application No. 10 014 128.2.

Office Action, dated Jun. 23, 2011, from Japanese Application No. 2007-541495.

Third Party Opposition, dated May 20, 2014, against European Patent EP 1824987 (Application No. 05851809.3), 18 pages.

Chung, et al.; "Integrin $\alpha_{IIb}\beta_3$-specific synthetic human monoclonal antibodies and HCDR3 peptides that potently inhibit platelet aggregation"—The FASEB Journal: Official Publication of the Federation of American Societies for Experimental Biology Feb. 2004, vol. 18, No. 2, Feb. 2004, pp. 361-363.

Extended European Search report dated Jun. 18, 2019 in respect of EP Appln No. 19169135.1.

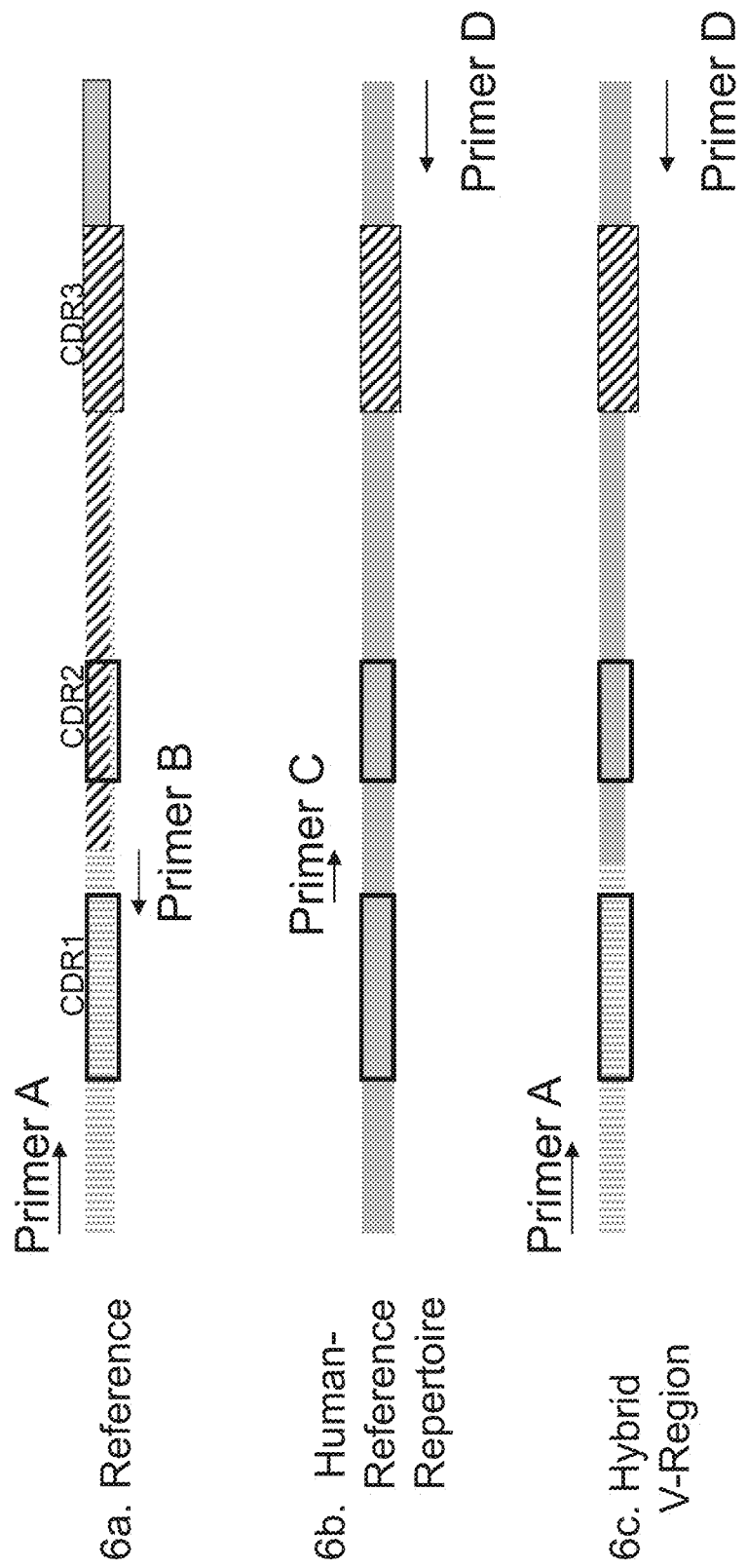

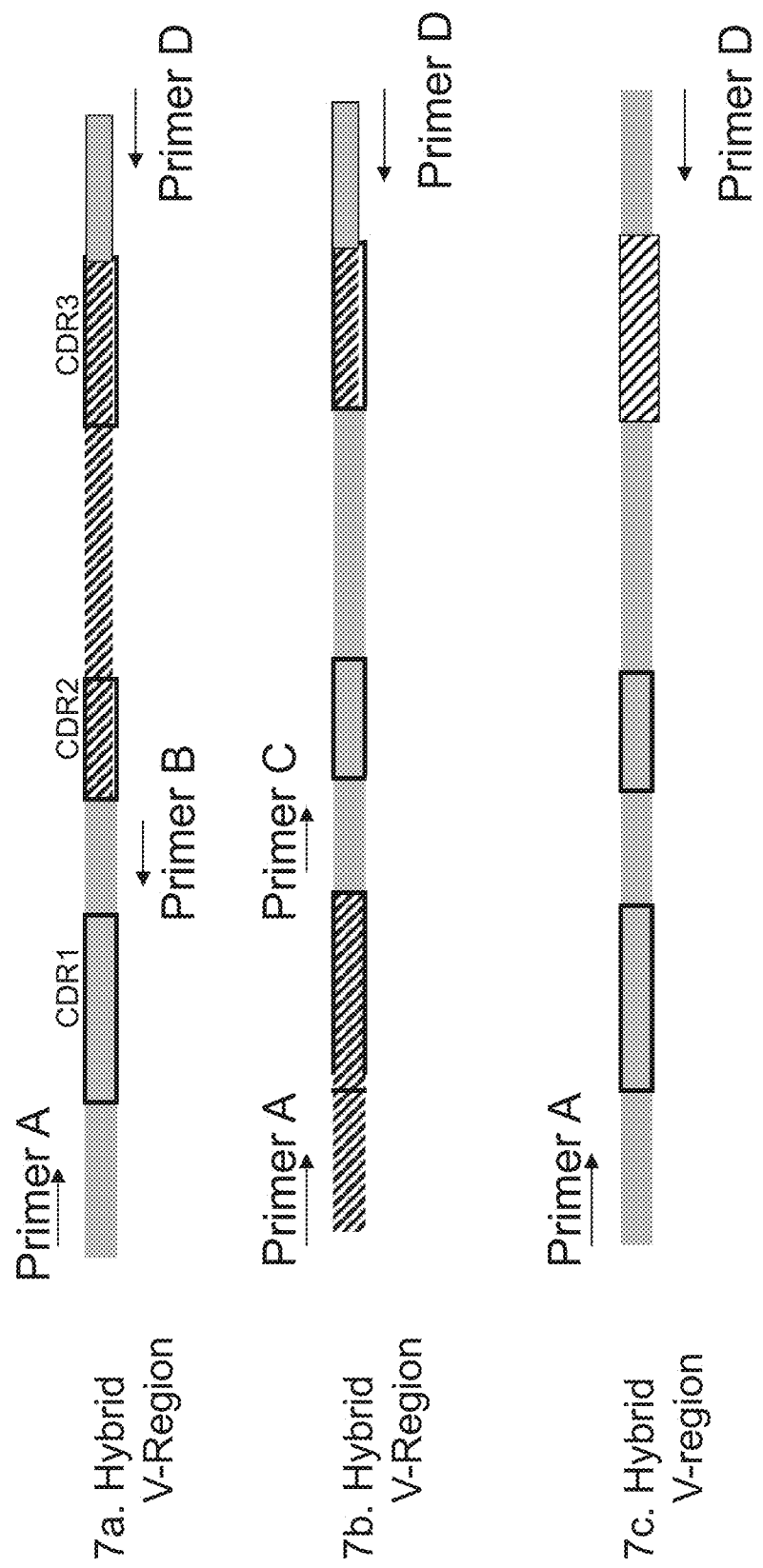

SEQUENCE LISTING

<160> NUMBER OF SEQ ID NOS: 20

<210> SEQ ID NO 1
<211> LENGTH: 14
<212> TYPE: PRT
<213> ORGANISM: Homo sapiens
<220> FEATURE:
<221> NAME/KEY: PEPTIDE
<222> LOCATION: (1)...(14)
<223> OTHER INFORMATION: human germline heavy chain variable domain
      (V-H) sub-class VH1 framework-2 region (FR2) consensus sequence

<400> SEQUENCE: 1

Trp Val Arg Gln Ala Pro Gly Gln Gly Leu Glu Trp Met Gly
1               5                   10

<210> SEQ ID NO 2
<211> LENGTH: 14
<212> TYPE: PRT
<213> ORGANISM: Homo sapiens
<220> FEATURE:
<221> NAME/KEY: PEPTIDE
<222> LOCATION: (1)...(14)
<223> OTHER INFORMATION: human germline heavy chain variable domain
      (V-H) sub-class VH1 framework-2 region (FR2)

<400> SEQUENCE: 2

Trp Val Arg Gln Ala Pro Gly Gln Arg Leu Glu Trp Met Gly
1               5                   10

<210> SEQ ID NO 3
<211> LENGTH: 14
<212> TYPE: PRT
<213> ORGANISM: Homo sapiens
<220> FEATURE:
<221> NAME/KEY: PEPTIDE
<222> LOCATION: (1)...(14)
<223> OTHER INFORMATION: human germline heavy chain variable domain
      (V-H) sub-class VH1 framework-2 region (FR2)

<400> SEQUENCE: 3

Trp Val Arg Gln Ala Thr Gly Gln Gly Leu Glu Trp Met Gly
1               5                   10

<210> SEQ ID NO 4
<211> LENGTH: 14
<212> TYPE: PRT
<213> ORGANISM: Homo sapiens
<220> FEATURE:
<221> NAME/KEY: PEPTIDE
<222> LOCATION: (1)...(14)
<223> OTHER INFORMATION: human germline heavy chain variable domain
      (V-H) sub-class VH1 framework-2 region (FR2)

<400> SEQUENCE: 4

Trp Val Arg Gln Ala Pro Gly Lys Gly Leu Glu Trp Met Gly
1               5                   10

<210> SEQ ID NO 5
<211> LENGTH: 14
<212> TYPE: PRT
<213> ORGANISM: Homo sapiens
<220> FEATURE:
<221> NAME/KEY: PEPTIDE
<222> LOCATION: (1)...(14)
<223> OTHER INFORMATION: human germline heavy chain variable domain
      (V-H) sub-class VH1 framework-2 region (FR2)

<400> SEQUENCE: 5

Trp Val Arg Gln Ala Pro Gly Gln Ala Leu Glu Trp Met Gly
1               5                   10

<210> SEQ ID NO 6
<211> LENGTH: 14
<212> TYPE: PRT
<213> ORGANISM: Homo sapiens
<220> FEATURE:
<221> NAME/KEY: PEPTIDE
<222> LOCATION: (1)...(14)
<223> OTHER INFORMATION: human germline heavy chain variable domain
      (V-H) sub-class VH1 framework-2 region (FR2)

<400> SEQUENCE: 6

Trp Val Arg Gln Ala Arg Gly Gln Arg Leu Glu Trp Ile Gly
1               5                   10

<210> SEQ ID NO 7
<211> LENGTH: 14
<212> TYPE: PRT
<213> ORGANISM: Homo sapiens
<220> FEATURE:
<221> NAME/KEY: PEPTIDE
<222> LOCATION: (1)...(14)
<223> OTHER INFORMATION: human germline heavy chain variable domain
      (V-H) sub-class VH1 framework-2 region (FR2)

<400> SEQUENCE: 7

Trp Val Gln Gln Ala Pro Gly Lys Gly Leu Glu Trp Met Gly
1               5                   10

<210> SEQ ID NO 8
<211> LENGTH: 14
<212> TYPE: PRT
<213> ORGANISM: Homo sapiens
<220> FEATURE:
<221> NAME/KEY: PEPTIDE
<222> LOCATION: (1)...(14)
<223> OTHER INFORMATION: human germline heavy chain variable domain
      (V-H) sub-class VH2 framework-2 region (FR2) consensus sequence

<400> SEQUENCE: 8

Trp Ile Arg Gln Pro Pro Gly Lys Ala Leu Glu Trp Leu Ala
1               5                   10

<210> SEQ ID NO 9
<211> LENGTH: 14
<212> TYPE: PRT
<213> ORGANISM: Homo sapiens
<220> FEATURE:
<221> NAME/KEY: PEPTIDE
<222> LOCATION: (1)...(14)
<223> OTHER INFORMATION: human germline heavy chain variable domain
      (V-H) sub-class VH3 framework-2 region (FR2)

<400> SEQUENCE: 9

Trp Val Arg Gln Ala Pro Gly Lys Gly Leu Glu Trp Val Ala
1               5                   10

<210> SEQ ID NO 10
<211> LENGTH: 14
<212> TYPE: PRT
<213> ORGANISM: Homo sapiens
<220> FEATURE:
<221> NAME/KEY: PEPTIDE
<222> LOCATION: (1)...(14)
<223> OTHER INFORMATION: human germline heavy chain variable domain
      (V-H) sub-class VH3 framework-2 region (FR2) consensus sequence

<400> SEQUENCE: 10

Trp Val Arg Gln Ala Pro Gly Lys Gly Leu Glu Trp Val Ser
1               5                   10

<210> SEQ ID NO 11
<211> LENGTH: 14
<212> TYPE: PRT
<213> ORGANISM: Homo sapiens
<220> FEATURE:
<221> NAME/KEY: PEPTIDE
<222> LOCATION: (1)...(14)
<223> OTHER INFORMATION: human germline heavy chain variable domain
      (V-H) sub-class VH3 framework-2 region (FR2)

<400> SEQUENCE: 11

Trp Ile Arg Gln Ala Pro Gly Lys Gly Leu Glu Trp Val Ser
1               5                   10

<210> SEQ ID NO 12
<211> LENGTH: 14
<212> TYPE: PRT
<213> ORGANISM: Homo sapiens
<220> FEATURE:
<221> NAME/KEY: PEPTIDE
<222> LOCATION: (1)...(14)
<223> OTHER INFORMATION: human germline heavy chain variable domain
      (V-H) sub-class VH3 framework-2 region (FR2)

<400> SEQUENCE: 12

Trp Val Arg Gln Ala Thr Gly Lys Gly Leu Glu Trp Val Ser
1               5                   10

<210> SEQ ID NO 13
<211> LENGTH: 14
<212> TYPE: PRT
<213> ORGANISM: Homo sapiens
<220> FEATURE:
<221> NAME/KEY: PEPTIDE
<222> LOCATION: (1)...(14)
<223> OTHER INFORMATION: human germline heavy chain variable domain
      (V-H) sub-class VH3 framework-2 region (FR2)

<400> SEQUENCE: 13

Trp Val Arg Gln Ala Pro Gly Lys Gly Leu Glu Trp Val Gly
1               5                   10

<210> SEQ ID NO 14
<211> LENGTH: 14
<212> TYPE: PRT
<213> ORGANISM: Homo sapiens
<220> FEATURE:
<221> NAME/KEY: PEPTIDE
<222> LOCATION: (1)...(14)
<223> OTHER INFORMATION: human germline heavy chain variable domain
      (V-H) sub-class VH3 framework-2 region (FR2)

<400> SEQUENCE: 14

Trp Phe Arg Gln Ala Pro Gly Lys Gly Leu Glu Trp Val Gly
1               5                   10

<210> SEQ ID NO 15
<211> LENGTH: 14
<212> TYPE: PRT
<213> ORGANISM: Homo sapiens
<220> FEATURE:
<221> NAME/KEY: PEPTIDE
<222> LOCATION: (1)...(14)
<223> OTHER INFORMATION: human germline heavy chain variable domain
      (V-H) sub-class VH3 framework-2 region (FR2)

```
<400> SEQUENCE: 15

Trp Val Arg Gln Ala Pro Gly Lys Gly Leu Glu Tyr Val Ser
1               5                   10

<210> SEQ ID NO 16
<211> LENGTH: 14
<212> TYPE: PRT
<213> ORGANISM: Homo sapiens
<220> FEATURE:
<221> NAME/KEY: PEPTIDE
<222> LOCATION: (1)...(14)
<223> OTHER INFORMATION: human germline heavy chain variable domain
      (V-H) sub-class VH3 framework-2 region (FR2)

<400> SEQUENCE: 16

Trp Val Arg Gln Ala Ser Gly Lys Gly Leu Glu Trp Val Gly
1               5                   10

<210> SEQ ID NO 17
<211> LENGTH: 14
<212> TYPE: PRT
<213> ORGANISM: Homo sapiens
<220> FEATURE:
<221> NAME/KEY: PEPTIDE
<222> LOCATION: (1)...(14)
<223> OTHER INFORMATION: human germline heavy chain variable domain
      (V-H) sub-class VH3 framework-2 region (FR2)

<400> SEQUENCE: 17

Trp Val Arg Gln Ala Pro Gly Lys Gly Leu Val Trp Val Ser
1               5                   10

<210> SEQ ID NO 18
<211> LENGTH: 14
<212> TYPE: PRT
<213> ORGANISM: Homo sapiens
<220> FEATURE:
<221> NAME/KEY: PEPTIDE
<222> LOCATION: (1)...(14)
<223> OTHER INFORMATION: human germline heavy chain variable domain
      (V-H) sub-class VH4 framework-2 region (FR2)

<400> SEQUENCE: 18

Trp Val Arg Gln Pro Pro Gly Lys Gly Leu Glu Trp Ile Gly
1               5                   10

<210> SEQ ID NO 19
<211> LENGTH: 14
<212> TYPE: PRT
<213> ORGANISM: Homo sapiens
<220> FEATURE:
<221> NAME/KEY: PEPTIDE
<222> LOCATION: (1)...(14)
<223> OTHER INFORMATION: human germline heavy chain variable domain
      (V-H) sub-class VH4 framework-2 region (FR2) consensus sequence

<400> SEQUENCE: 19

Trp Ile Arg Gln Pro Pro Gly Lys Gly Leu Glu Trp Ile Gly
1               5                   10

<210> SEQ ID NO 20
<211> LENGTH: 14
<212> TYPE: PRT
<213> ORGANISM: Homo sapiens
<220> FEATURE:
<221> NAME/KEY: PEPTIDE
<222> LOCATION: (1)...(14)
<223> OTHER INFORMATION: human germline heavy chain variable domain
      (V-H) sub-class VH4 framework-2 region (FR2)
```

```
<400> SEQUENCE: 20

Trp Ile Arg Gln His Pro Gly Lys Gly Leu Glu Trp Ile Gly
1               5                   10
```

IMMUNOGLOBULIN VARIABLE REGION CASSETTE EXCHANGE

CROSS-REFERENCE TO RELATED APPLICATIONS

This application is a continuation of U.S. patent application Ser. No. 11/282,107 filed Oct. 13, 2011, which claims benefit of U.S. provisional application No. 60/628,581 filed Nov. 16, 2004, each of which applications is incorporated by reference herein.

REFERENCE TO A SEQUENCE LISTING

This application includes a Sequence Listing as a text file named "SEQ_0967001.txt" created Dec. 11, 2015, and containing 7,227 bytes. The material contained in this text file is incorporated by reference in its entirety for all purposes.

BACKGROUND OF THE INVENTION

The antigen-binding moieties of antibodies are typically comprised of two immunoglobulin domains, a heavy chain variable ($V_H$) domain and a light chain variable ($V_L$) domain. Each domain has three loops of variable sequence which form the complementarity determining regions (CDRs). The six CDRs (three from $V_H$ and three from $V_L$) extend from one face of the variable region structure to form the antigen binding site. In most antibodies, appropriate association of the two chains is required to bind antigen with significant affinity. Thus a $V_H$ and $V_L$ domain together form the minimum antigen-binding unit.

Widespread use has been made of monoclonal antibodies, particularly those derived from rodents including mice. However they frequently raise an immune response in human clinical use (e.g., Miller, R. A. et al., *Blood* 62:988-995 (1983); Schroff, R. W. et al., *Cancer Res.* 45:879-885 (1985)). The art has attempted to overcome this problem by constructing "chimeric" antibodies in which an animal antigen-binding variable domain is coupled to a human constant domain (U.S. Pat. No. 4,816,567; Morrison, S. L. et al., *Proc. Natl. Acad. Sci. USA* 81:6851-6855 (1984); Boulianne, G. L. et al., *Nature* 312:643-646 (1984); Neuberger, M. S. et al., *Nature* 314:268-270 (1985)).

In a further effort to minimize the use of heterologous sequences in human antibodies, a number of humanization approaches have been described (e.g., Jones, P. T. et al. *Nature* 321:522-525 (1986); Riechmann, L. et al., *Nature* 332:323-327 (1988); Verhoeyen, M. et al., *Science* 239:1534-1536 (1988); Queen et al, *Proc Natl Acad Sci USA*. 86:10029-33 (1989); U.S. Pat. Nos. 5,693,762, and 5,585,089). In such techniques, CDRs from a donor immunoglobulin are inserted into a human framework. Typically, additional residues in the frameworks of the human acceptor antibody are also substituted with rodent residues to preserve the native conformation of the rodent CDRs necessary to recover full binding activity. Thus, humanized antibodies often retain six CDRs from the rodent antibody and several additional rodent residues in the framework regions. By transferring the six CDRs from the rodent antibody to human frameworks, the specificity of the starting antibody is typically retained in the humanized antibody but the affinity of the humanized antibody is, in many cases, reduced compared with the starting antibody. Consequently, several iterations of the humanization process may be required, in which alternative combinations of back-mutations in the framework regions are constructed and tested, in order to obtain adequate binding affinities. Even after multiple iterations, it is not always possible to identify CDR-grafted antibodies with affinities equivalent to the starting antibody.

Human antibodies have also been isolated in vitro by expression of repertoires of antibody genes in microbial expression systems. A number of display technologies exist in which the expressed antibody fragments are presented as fusion proteins tethered to the surface of a microbial cell or a bacteriophage. The phage or host cell serves as a replicable genetic display package (rgdp) and rgdps which bind to a specified antigen can be selected and expanded in culture to isolate genes encoding antibodies against the selecting antigen. Antibody fragments can be isolated in this way from expression on the surface of yeast (Feldhaus et al., *Nat Biotechnol.* 21:163-70, 2003), bacterial cells (Daugherty et al., *Protein Eng.* 12:613-21, 1999) or, most commonly, on phage. Phage display allows large combinatorial libraries to be screened for rare antigen-binding antibodies (Hoogenboom and Winter, *J Mol Biol.* 227:381, 1992; Marks et al., *J Mol Biol.* 222:581, 1991; Winter et al., *Annu Rev Immunol.* 12:433-55, 1994). Large combinatorial libraries of potential binders can be created from two smaller libraries for selection of the desired combination. For example, a first library of $10^7$ H chains can be created and displayed on a bacteriophage. A second library of $10^7$ L chains, in which the coding sequences for these light chains are within a plasmid vector, are expressed in the periplasmic space of a host bacterium. The H-chain and L-chain libraries are combined to provide $10^{14}$ combinations of H and L chains on the surface of the resulting phage in the bacterial supernatant.

Various methods of increasing diversity in phage-antibody libraries are known in the art. One such method involves combining random assortments of germline-encoded CDR sequences into a set of human framework regions in order to generate artificial libraries of human antibodies ("CDR shuffling"). See, e.g., Jirholt et al., *Gene* 215: 471, 1998; Soderlind et al., *Nat Biotechnol.* 18:852-6, 2000).

Phage display can also be used to identify human antibodies with the binding specificity of a rodent antibody by a two-step process of guided selection in which a library of human $V_L$ chains is paired with the $V_H$ chain of the rodent antibody and half-human antibodies are selected for antigen binding. The identified human chains are then paired with a library of human $V_H$ chains in order to identify human $V_H$-$V_L$ pairs capable of binding antigen (e.g., U.S. Pat. No. 5,565,332; Jespers, et al., *Bio/Technology* 12:899-903, 1994; Beiboer et al., *J Mol Biol.* 296:833-49, 2000). In some cases the heavy chain CDR3 of the rodent antibody is retained in the guided selection (Klimka et al., *Br J Cancer* 83:252-60, 2000) In other cases, both the CDRH3 and CDRL3 of the rodent antibody are retained in the final humanized antibody after guided selection (e.g., Rader et al., *Proc Natl Acad Sci USA*. 95:8910-5, 1998).

In all of these cases large, high diversity libraries are typically used in order to identify antibodies with high affinities. The human antibodies derived from the technologies in the art therefore tend to have a significant number of amino acid differences from the closest germ-line sequence. Such somatic mutation contributes to the generation of high affinity antibodies in natural antibodies (e.g., England et al., *J. Immunol.* 162:2129, 1999) and has generally been regarded as important for the generation of high affinity antibodies in antibodies generated from in vitro libraries. However, such mutations generate new protein sequences that may be recognized as foreign by the body's immune system. The immune system is expected to be unresponsive ("tolerant") to immunoglobulins expressed broadly during development, i.e., sequences found in the germ-line, unmutated form, but mutations in these sequences can allow the immune system to distinguish these as foreign proteins. Thus antibodies with numerous differences from germ-line sequences may be expected to be immunogenic when used therapeutically in humans.

There is therefore a need for improved methods for humanizing rodent antibodies in order to further reduce the potential for immunogenicity while retaining the specificity and binding affinity of the starting antibody. There is a also need for methods for identifying human antibodies with the specificity of a starting reference antibody, e.g., a mouse antibody, but which utilize human immunoglobulin sequences that are germ-line or close to germ-line. The invention addresses this need.

The invention further provides solutions to problems of reliability inherent in antibody humanization technologies including chain-guided selection and CDR-grafting. CDR-grafting technologies provide antibodies with human $V_H$ and $V_L$ framework sequences but that retain significant portions of the variable region of the reference antibody. These may have reduced affinity compared with the starting antibody, and can be laborious to produce by multiple iterative genetic engineering steps. The current invention provides methods of engineering a reference antibody to provide a humanized antibody that retains affinity for the target antigen.

BRIEF SUMMARY OF THE INVENTION

The current invention provides methods for generating engineered antibodies with the specificity of a reference antibody by replacement of portions of the $V_H$ and $V_L$ sequences of the reference antibody with sequences from human antibody repertoires. The invention also provides novel compositions comprising hybrid immunoglobulin variable domains containing a combination of frameworks (FRs) and CDRs from different antibody clones. Further, the invention provides libraries of hybrid V-regions.

Thus, in one aspect, the invention provides a method of engineering an antibody that retains the binding specificity of a reference antibody for a target antigen, the method comprising: (a) obtaining a heavy chain or a light chain variable region from the reference antibody; (b) replacing at least one exchange cassette of a V gene segment of the variable region with a library of corresponding exchange cassettes from human V-gene segments, thereby generating a library of hybrid V-regions, with the proviso that the exchange cassette has less than three framework regions, (c) pairing the library of hybrid V regions of (b) with a complementary V-region; and (d) selecting an antibody comprising a hybrid V region that has a binding affinity for the target antigen. The exchange cassette is generally selected from the group consisting of FR1-CDR1, FR1-CDR1-FR2, FR2-CDR2-FR3, CDR2-FR3, CDR1-FR2, CDR1-FR2-CDR2, CDR1-FR2-CDR2-FR3, FR1-CDR1-FR2-CDR2, and FR2-CDR2. Often, the exchange cassette is selected from the group consisting of FR1-CDR1, FR1-CDR1-FR2, FR2-CDR2-FR3, and CDR2-FR3. In some embodiments, at least one CDR sequence or FR sequence of the exchange cassette is a partial CDR. In other embodiments, at least one FR sequence can be a partial FR sequence. Further, at least one of the human exchange cassettes can be a human germline sequence. The antibody that is selected can be an Fv fragment, an Fab, an Fab', an F(ab')2, an scFv, or another fragment of an immunoglobulin, such as a fragment that is deleted in CH2 or CH3.

The method can also comprise additional steps of: (e) replacing a second exchange cassette of the V region with a library of corresponding exchange cassettes from human V-gene segments to create a second hybrid library of hybrid V regions; (f) pairing the second library of hybrid V regions with a complementary V-region; (g) selecting an antibody comprising a second hybrid V region, which antibody has a binding affinity for the target antigen, and (h) combining the human exchange cassette of the antibody of (d) with the second human exchange cassette of the antibody of (g), to obtain an antibody with the binding specificity of the reference antibody that has at least two human exchange cassettes. These steps can be performed concurrently with (b) through (d); or sequentially, in any order relative to steps (b) through (d). The second cassette can also have at least one CDR sequence or FR sequence that is a partial CDR sequence or FR sequence.

In some embodiments, the method further comprises a step of replacing the CDR3-FR4 of a hybrid variable region with a library of CDR3-FR4 regions, pairing the variable region with a complementary variable region, and selecting an antibody that has a high binding affinity to the target antigen.

The complementary V region of (c) or (f) can be, for example, a V region that comprises a naturally occurring V-segment, a hybrid V-region, or a hybrid V region that is a member of a library that comprises different hybrid V-regions.

In some embodiments of the invention, antibodies comprising one or more hybrid V-regions are expressed and secreted in soluble form from a host cell, e.g., a prokaryotic cell, a yeast, or a mammalian cell, and bind to an antigen.

In an alternative embodiments, an antibody comprising a hybrid V-region is displayed on a cell, a spore, or a virus.

In an exemplary cassette exchange procedure, the invention provides a method of engineering an antibody comprising: (a) obtaining a variable region (either a heavy chain or a light chain variable region) of a reference antibody having a desired binding specificity; (b) replacing the FR1-CDR1-FR2 of the variable region of the reference antibody with a library of human FR1-CDR1-FR2 regions to create a library of hybrid variable regions, pairing the hybrid variable regions with a complementary variable region, and selecting an antibody having a detectable affinity for the target antigen; (c) replacing the FR2-CDR2-FR3 of the variable region of the reference antibody with a library of human FR2-CDR2-FR3 regions to create a library of hybrid variable regions, pairing the hybrid variable regions with a complementary variable region, and selecting an antibody having a detectable affinity for the target antigen; (d) combining the FR1-CDR1-FR2 of the hybrid variable region of the antibody selected in (b) with the FR2-CDR2-FR3 of the hybrid variable region of the antibody selected in (c) to obtain an antibody with a human variable region V segment, which antibody has the binding specificity of the reference antibody. In one embodiment, the FR2 sequence or FR3 sequence is a partial FR sequence. In further embodiments, the FR1-CDR1-FR2 and/or the FR2-CDR2-FR3 is from a library of human germline sequences.

The steps of the method can be performed concurrently or sequentially. Further, when performed sequentially, steps (b) and (c) can be performed in any order.

The complementary V region of (b) or (c) can be, for example, a V region that comprises a naturally occurring V-segment, a hybrid V-region, or a hybrid V region that is a member of a library that comprises different hybrid V-regions.

In one embodiment, the step of combining the FR1-CDR1-FR2 with the FR2-CDR2-FR3 comprises combining the FR2 regions in a region of homology, i.e., the FR1-CDR1-FR2 and the FR2-CDR2-FR3 are combined in an area that has sequence identity, e.g., at least 70%, 75%, 80%, 85%, or 90% or greater, identity, in the FR2 region. "Combining" can take place, e.g., through recombination.

Alternatively, combining the FR1-CDR1-FR2 with the FR2-CDR2-FR3 comprises replacing the FR2 from FR1-CDR1-FR2 with the FR2 from FR2-CDR2-FR3, or replacing the FR2 from FR2-CDR2-FR3 with the FR2 from FR1-CDR1-FR2.

The method set forth above can also comprise an additional step of replacing the CDR3-FR4 of a hybrid variable region comprising at least one human V segment, supra, with a library of human CDR3-FR4 regions, pairing the variable region with a complementary variable region, and selecting an antibody that binds to the target antigen.

In another embodiment, the method can comprise replacing the -FR3-CDR3-FR4 of a hybrid variable region comprising at least one human V segment, supra, with a library of FR3-CDR3-FR4 regions, pairing the variable region with a complementary variable region, and selecting an antibody has a detectable affinity for the target antigen. The embodiment further comprises combining the FR3-CDR4-FR4 of the hybrid variable region of the antibody selected above with the FR2-CDR2-FR3 of the hybrid variable region of the antibody selected in (d) to obtain an antibody with these human variable region V segments, which antibody has the binding specificity of the reference antibody.

In another exemplary antibody engineering procedure of the invention, the method comprises:
(a) obtaining a variable region of a reference antibody having a desired binding specificity:
(b) replacing the FR1-CDR1-FR2 of the variable region of the reference antibody with a library of human FR1-CDR1-FR2 regions to create a library of hybrid variable regions, pairing the hybrid variable regions with a complementary variable region, and selecting an antibody having a detectable affinity for the target antigen:
(c) replacing the CDR2-FR3 of the variable region of the reference antibody with a library of human CDR2-FR3 regions to create a library of hybrid variable regions, wherein the CDR2 of the CDR2-FR3 of the reference antibody is a partial CDR2 and the library of human CDR2-FR3 sequences comprise corresponding partial CDR2-FR3 sequences, pairing the hybrid variable regions with a complementary variable region, and selecting an antibody having a detectable affinity for the target antigen, and
(d) combining the FR1-CDR1-FR2 of the hybrid variable region of the antibody selected in (b) with the CDR2-FR3 of the hybrid variable region of the antibody selected in (c) to obtain an antibody with a human variable region V segment, which antibody has the binding specificity of the reference antibody. In some embodiments, the method also comprises a step of replacing the CDR3-FR4 of the reference antibody with a library of human CDR3-FR4 regions, pairing the variable region with a complementary variable region, and selecting an antibody that binds to the target antigen. The CDR3 regions of the library of human CDR3-FR4 can be complete CDR3 regions or partial CDR3 regions.

In an alternative embodiments, the exemplary method further comprises: (e) replacing the FR4 of the variable region of the starting reference antibody or engineered antibody with a library of FR4 regions, pairing the variable region with a complementary variable region, and selecting an antibody has a detectable affinity for the target antigen.

In another aspect, the invention provides an engineered antibody having the binding specificity of a reference antibody, e.g., a nonhuman antibody, the engineered antibody comprising: a variable domain comprising a V-gene segment having a human exchange cassette from one human antibody gene and a second exchange cassette from a different antibody gene; wherein the first and the second exchange cassettes each have at least one framework joined in natural order to one CDR, with the proviso that the exchange cassette has less than three framework regions; and a CDR3 and FR4 from a reference antibody. In some embodiments, the first and/or the second exchange cassette is a human germline sequence.

The invention also provides an engineered antibody having the binding specificity of a reference antibody, e.g., a nonhuman reference antibody, the engineered antibody comprising: a variable domain comprising a V-gene segment having a human exchange cassette from one human antibody gene and a second exchange cassette from a different human antibody gene, with the proviso that the exchange cassettes have less than three framework regions; and at least a partial CDR3 sequence from a reference antibody, and an FR4 sequence from the reference antibody or a human FR4 sequence. In some embodiments, the partial CDR3 sequence from the reference antibody is the minimal essential binding specificity determinant (MEBSD) of the CDR3. Often, the partial CDR3 sequence has a D segment from the reference antibody. Such an engineered antibody typically has a human FR4 sequence, e.g., a human germline FR4 sequence.

In another aspect, the invention provides an engineered antibody in which at least one FR3 of a reference antibody has been replaced with a human FR3. The FR3 can be the heavy or light chain FR3. In some embodiments, both the heavy and light chain FR3 regions are replaced.

In another aspect, the invention provided libraries of hybrid V-regions. A library of hybrid V-regions of the invention comprises members that have different V-regions. A hybrid V-region in the library has at least a partial CDR, e.g., an MEBSD, from a reference antibody and at least one exchange cassette from a human repertoire, with the proviso that the exchange cassette has less than three framework regions. At least one of the CDR sequences and/or at least one of the FR sequences of the exchange cassette can be a partial CDR sequence or FR sequence. The exchange cassette can be, e.g. FR1-CDR1. FR1-CDR1-FR2, FR2-CDR2-FR3, or CDR2-FR3. In some embodiments, the exchange cassette is a human germline sequence.

The member of the library can have at least two exchange cassettes from a human repertoire.

In typical embodiments, the CDR, or partial CDR, from the reference antibody that is present in the members of the library is a CDR3 sequence. Further, the library members often have a human FR4 sequence, which can be the same sequence or different sequences in various members of the library. Typically, the partial CDR3 is an MEBSD and/or the D segment from the reference antibody.

In yet another aspect, the invention provides a method of engineering an antibody comprising a $V_H$ dimer that retains the binding specificity of a reference antibody. Such methods employ exchange cassettes as described herein, however, during the generation of the antibody, there is no step of pairing the hybrid $V_H$ region with a complementary $V_L$ region. Thus, the method typically comprises (a) obtaining a heavy chain variable region from the reference antibody, e.g., a camelid reference antibody; (b) replacing at least one exchange cassette of a V gene segment of the variable region with a library of corresponding exchange cassettes from human V-gene segments, thereby generating a library of hybrid V-regions, with the proviso that the exchange cassette has less than three framework regions, and (d) selecting an antibody comprising a hybrid V region that has a binding affinity for the target antigen. The exchange cassette is generally selected from the group consisting of FR1-CDR1, FR1-CDR1-FR2, FR2-CDR2-FR3, CDR2-FR3, CDR1-FR2, CDR1-FR2-CDR2, CDR1-FR2-CDR2-FR3, FR1-CDR1-FR2-CDR2, and FR2-CDR2. Often, the exchange cassette is selected from the group consisting of FR1-CDR1, FR1-CDR1-FR2, FR2-CDR2-FR3, and CDR2-FR3. In some embodiments, at least one CDR sequence or FR sequence of the exchange cassette is a partial CDR sequence or FR sequence. Such an antibody can be expressed, e.g., in a host cell such as a prokaryotic cell, a yeast, or a mammalian cell, or can be displayed on the surface of a cell, a spore or a virus.

BRIEF DESCRIPTION OF THE DRAWINGS

FIG. 6a-6c provides a schematic showing an iterative exchange cassette construction.

FIG. 7a-7c provides a schematic showing a cassette reconstruction.

DETAILED DESCRIPTION OF THE INVENTION

Definitions

Figure 1:
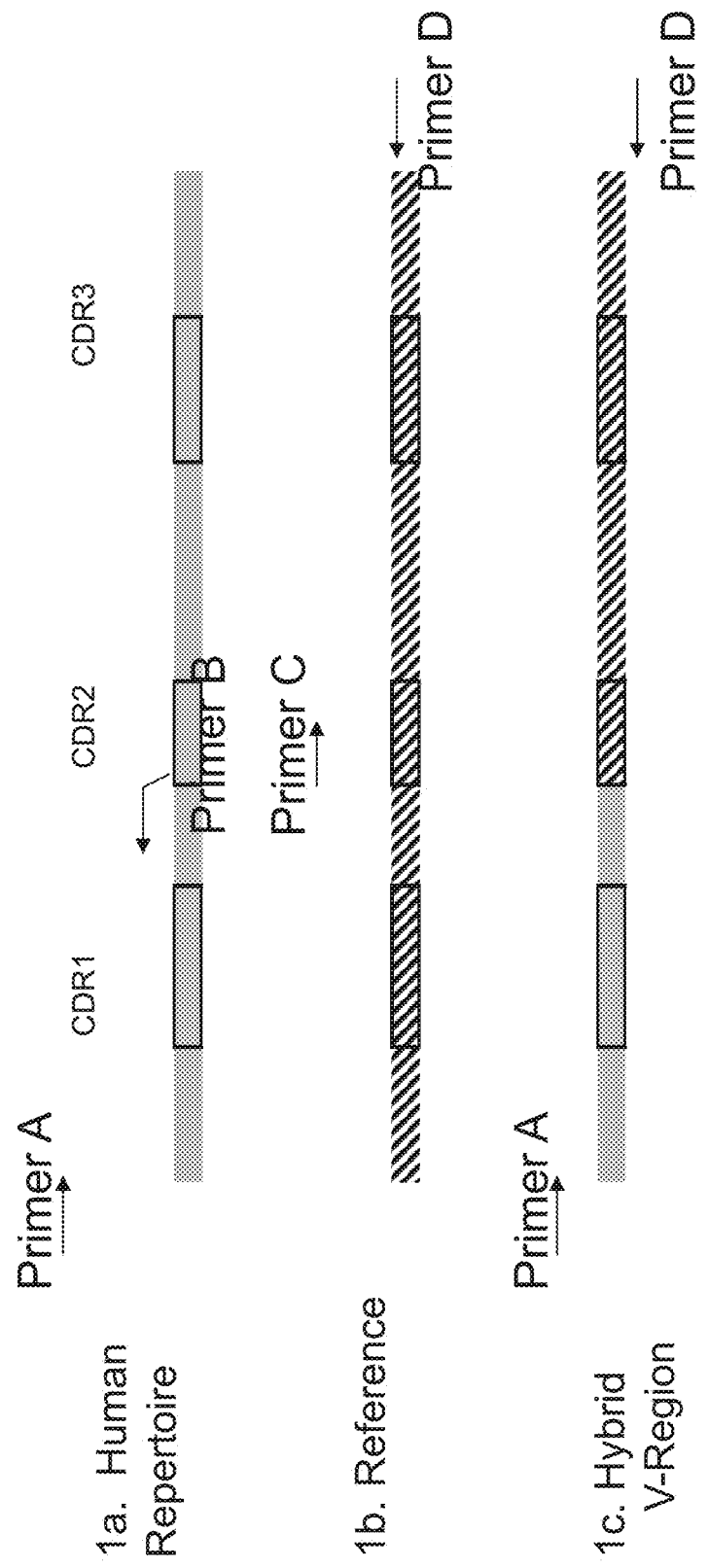
FIG. 1a-1c provides a schematic showing an exchange cassette replacement of a FR1-CDR1-FR2 cassette in a reference antibody.

As used herein, an "antibody" refers to a protein functionally defined as a binding protein and structurally defined as comprising an amino acid sequence that is recognized by one of skill as being derived from the framework region of an immunoglobulin encoding gene of an animal producing antibodies. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody, as used herein also includes antibody fragments either produced by the modification of whole antibodies or synthesized using recombinant DNA methodologies. Preferred antibodies include $V_H$-$V_L$ dimers, including single chain antibodies (antibodies that exist as a single polypeptide chain), such as single chain Fv antibodies (sFv or scFv) in which a variable heavy and a variable light region are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker (e.g., Huston, et al. *Proc. Nat. Acad. Sci. USA,* 85:5879-5883, 1988). While the $V_H$ and $V_L$ are connected to each as a single polypeptide chain, the $V_H$ and $V_L$ domains associate non-covalently. Alternatively, the antibody can be another fragment. Other fragments can also be generated, including using recombinant techniques. For example Fab molecules can be displayed on phage if one of the chains (heavy or light) is fused to g3 capsid protein and the complementary chain exported to the periplasm as a soluble molecule. The two chains can be encoded on the same or on different replicons; the two antibody chains in each Fab molecule assemble post-translationally and the dimer is incorporated into the phage particle via linkage of one of the chains to g3p (see. e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). Particularly preferred antibodies include all those that have been displayed on phage or generated by recombinant technology using vectors where the chains are secreted as soluble proteins, e.g., scFv, Fv. Fab, pr (Fab')2 or generated by recombinant technology using vectors where the chains are secreted as soluble proteins. Antibodies can also include diantibodies and miniantibodies.

Antibodies of the invention also include heavy chain dimers, such as antibodies from camelids. Since the VH region of a heavy chain dimer IgG in a camelid does not have to make hydrophobic interactions with a light chain, the region in the heavy chain that normally contacts a light chain is changed to hydrophilic amino acid residues in a camelid. VH domains of heavy-chain dimer IgGs are called VHH domains.

In camelids, the diversity of antibody repertoire is determined by the complementary determining regions (CDR) 1, 2, and 3 in the VH or VHH regions. The CDR3 in the camel VHH region is characterized by its relatively long length averaging 16 amino acids (Muyldermans et al., 1994, *Protein Engineering* 7(9): 1129). This is in contrast to CDR3 regions of antibodies of many other species. For example, the CDR3 of mouse $V_H$ has an average of 9 amino acids.

Libraries of camelid-derived antibody variable regions, which maintain the in vivo diversity of the variable regions of a camelid, can be made by, for example, the methods disclosed in United States Patent Application Ser. No. 20050037421, published Feb. 17, 2005.

"V-region" refers to an antibody variable region domain comprising the segments of Framework 1, CDR1, Framework 2, CDR2, and Framework 3, including CDR3 and Framework 4, which segments are added to the V-segment as a consequence of rearrangement of the heavy chain and light chain V-region genes during B-cell differentiation.

A "complementary variable region" refers to a region that can dimerise with a V-region to produce a functional binding fragment that specifically binds to an antigen of interest. A complementary variable region is typically a $V_L$ region, where the variable region is a $V_H$ region; or is a $V_H$ region, where the variable region is a $V_L$ region. The complementary variable region often comprises a CDR3 from a reference antibody that binds to the antigen of interest.

The term "V-segment" refers to the region of the V-region (heavy or light chain) that is encoded by a V gene. A "D-segment" refers to the region of a V-region (in this case, a CDR3 in the V-region) that is encoded by a D gene. Similarly, a "J-segment" refers to a region encoded by a J gene. These terms include various modifications, additions, deletions, and somatic mutations, that can occur during maturation.

An "exchange cassette" as used herein typically refers to at least one intact CDR adjoined to a at least one intact framework region that are together, naturally occurring. An "exchange cassette" also can refer to at least a part of one CDR that is adjoined to at least one framework that are, together, naturally occurring. In other embodiments, an exchange cassette refers to at least one CDR joined to at least a part of one FR that are together, naturally occurring. An "exchange cassette" can also comprise at least one partial CDR adjoined to at least one partial FR that are together, naturally occurring. An "exchange cassette" can also be isolated from a synthetic library in which one or more of the CDRs is mutated. In this case, the CDR prior to mutagenesis and framework region together are naturally occurring.

A "partial CDR" or "part of a CDR" or "partial CDR sequence" in the context of this invention refers to a subregion of an intact CDR sequence, e.g., the CDR region outside of the minimal essential binding site, that is present in an exchange cassette. An exchange cassette of this invention can thus have a "partial" CDR. The end result in the hybrid V-region is a hybrid CDR. For example, a CDR2-FR3 exchange cassette includes embodiments in which a subregion of the CDR2 sequence is present in the CDR2-FR3 exchange cassette such that a hybrid V-region resulting from a CDR2-FR3 exchange would have a CDR2 in which part of the CDR2 is from the exchanged cassette and part is from the CDR2 of the reference antibody. A "partial" CDR sequence comprises a subregion of contiguous residues that is at least 20%, typically at least 30%, 40%, 50%, 60%, 70%, 80%, or 90% or more of the intact CDR A "partial FR" or "part of a FR" or "partial FR sequence" in the context of this invention refers to a subregion of an intact FR that is present in an exchange cassette. Accordingly, an exchange cassette of the invention can have a "partial FR" such that a hybrid V-region that is generated from an exchange cassette that has a partial FR, has part of its FR sequence from the exchanged cassette and part of the FR from the V-region of the reference antibody. A "partial" FR sequence comprises a subregion of contiguous residues that is at least 20%, typically at least 20%, typically at least 30%, 40%, 50%, 60%, 70%, 80%, or 90% or more of the intact FR.

An "extended cassette" as used herein refers to an exchange cassette that comprises an additional framework region. Thus, here an "extended cassette" is an exchange cassette that has at least one CDR and at least two framework regions that are, together, naturally occurring. An "extended cassette" can also be isolated from a synthetic library in which one or more of the CDRs is mutated. In this case, the CDR prior to mutagenesis and framework region together are naturally occurring.

"Naturally occurring" as used in the context of exchange and extended cassettes means that the components are encoded by a single gene that was not altered by recombinant means and that pre-exists in an antibody library that was created from naive cells or cells that were exposed to an antigen.

A "corresponding" exchange cassette refers to a CDR and a framework region that is encoded by a different antibody gene or gene segment (relative to an antibody that is to undergo exchange), but is, in terms of general antibody structure, the same CDR and framework region of the antibody. For example, a CDR1-FR1 exchange cassette is replaced by a "corresponding" CDR1-FR1 cassette that is encoded by a different antibody gene relative to the reference CDR1-FR1. The definition also applies to an exchange cassette having a partial CDR sequence and/or a partial FR region sequence.

A "hybrid V region" refers to a V-region in which at least one exchange cassette has been replaced by a corresponding exchange cassette from a different antibody gene or gene segment.

"Antigen" refers to substances that are capable, under appropriate conditions, of inducing a specific immune response and of reacting with the products of that response, that is, with specific antibodies or specifically sensitized T-lymphocytes, or both. Antigens may be soluble substances, such as toxins and foreign proteins, or particulates, such as bacteria and tissue cells; however, only the portion of the protein or polysaccharide molecule known as the antigenic determinant (epitopes) combines with the antibody or a specific receptor on a lymphocyte. More broadly, the term "antigen" may be used to refer to any substance to which an antibody binds, or for which antibodies are desired, regardless of whether the substance is immunogenic. For such antigens, antibodies may be identified by recombinant methods, independently of any immune response.

The "binding specificity" of an antibody refers to the identity of the antigen to which the antibody binds, preferably to the identity of the epitope to which the antibody binds.

"Chimeric polynucleotide" means that the polynucleotide comprises regions which are wild-type and regions which are mutated. It may also mean that the polynucleotide comprises wild-type regions from one polynucleotide and wild-type regions from another related polynucleotide.

"Complementarity-determining region" or "CDR" refer to the art-recognized term as exemplified by the Kabat and Chothia. CDRs are also generally known as hypervariable regions or hypervariable loops (Chothia and Lesk (1987). *J. Mol. Biol.* 196: 901; Chothia et al. (1989) *Nature* 342: 877; E. A. Kabat et al., *Sequences of Proteins of Immunological Interest* (National Institutes of Health, Bethesda, Md.) (1987); and Tramontano et al. (1990) *J. Mol. Biol.* 215: 175). "Framework region" or "FR" refers to the region of the V domain that flank the CDRs. The positions of the CDRs and framework regions can be determined using various well known definitions in the art, e.g., Kabat, Chothia, international ImMunoGeneTics database (IMGT), and AbM (see. e.g., Johnson et al., supra; Chothia & Lesk, 1987, Canonical structures for the hypervariable regions of immunoglobulins. *J. Mol. Biol.* 196, 901-917; Chothia C. et al., 1989, Conformations of immunoglobulin hypervariable regions. Nature 342, 877-883; Chothia C. et al., 1992, structural repertoire of the human VH segments J. Mol. Biol. 227, 799-817; Al-Lazikani et al., *J. Mol. Biol* 1997, 273(4)). Definitions of antigen combining sites are also described in the following: Ruiz et al., IMGT, the international ImMunoGeneTics database. *Nucleic Acids Res.*, 28, 219-221 (2000); and Lefranc, M.-P. IMGT, the international ImMunoGeneTics database. *Nucleic Acids Res.* January 1; 29(1): 207-9 (2001); MacCallum et al, Antibody-antigen interactions: Contact analysis and binding site topography, *J. Mol. Biol.*, 262 (5), 732-745 (1996); and Martin et al, *Proc. Natl Acad. Sci. USA,* 86, 9268-9272 (1989); Martin, et al, Methods Enzymol., 203, 121-153, (1991); Pedersen et al, *Immunomethods*, 1, 126, (1992); and Rees et al, In Sternberg M. J. E. (ed.), Protein Structure Prediction. Oxford University Press, Oxford, 141-172 1996).

"Epitope" refers to that portion of an antigen or other macromolecule capable of forming a binding interaction that interacts with the variable region binding pocket of an antibody. Typically, such binding interaction is manifested as an intermolecular contact with one or more amino acid residues of a CDR. Often, the binding involves a CDR3 or a CDR3 pair.

"Expression vector" includes vectors which are capable of expressing nucleic acid sequences contained therein, i.e., any nucleic acid sequence which is capable of effecting expression of a specified nucleic acid code disposed therein (the coding sequences are operably linked to other sequences capable of effecting their expression). Some expression vectors are replicable in the host organism either as episomes or as an integral part of the chromosomal DNA. A useful, but not a necessary, element of an effective expression vector is a marker encoding sequence—i.e. a sequence encoding a protein which results in a phenotypic property (e.g. tetracycline resistance) of the cells containing the protein which permits those cells to be readily identified. Expression vectors are frequently in the form of plasmids or viruses. However, the invention is intended to include such other forms of expression vectors which serve equivalent functions and which may, from time to time become known in the art.

"Homologs" means polypeptides having the same or conserved residues at a corresponding position in their primary, secondary or tertiary structure. The term also extends to two or more nucleotide sequences encoding the homologous polypeptides. Example homologous peptides are the immunoglobulin isotypes.

"Host cell" refers to a prokaryotic or eukaryotic cell into which the vectors of the invention may be introduced, expressed and/or propagated. A microbial host cell is a cell of a prokaryotic or eukaryotic micro-organism, including bacteria, yeasts, microscopic fungi and microscopic phases in the life-cycle of fungi and slime molds. Typical prokaryotic host cells include various strains of *E. coli*. Typical eukaryotic host cells are yeast or filamentous fungi, or mammalian cells, such as Chinese hamster ovary cells, murine NIH 3T3 fibroblasts, human embryonic kidney 193 cells, or rodent myeloma or hybridoma cells.

"Isolated" refers to a nucleic acid or polypeptide separated not only from other nucleic acids or polypeptides that are present in the natural source of the nucleic acid or polypeptide, but also from polypeptides, and preferably refers to a nucleic acid or polypeptide found in the presence of (if anything) only a solvent, buffer, ion, or other component normally present in a solution of the same. The terms "isolated" and "purified" do not encompass nucleic acids or polypeptides present in their natural source.

"Purified" means that the indicated nucleic acid or polypeptide is present in the substantial absence of other biological macromolecules, e.g., polynucleotides, proteins, and the like. In one embodiment, the polynucleotide or polypeptide is purified such that it constitutes at least 95% by weight, more preferably at least 99.8% by weight, of the indicated biological macromolecules present (but water, buffers, and other small molecules, especially molecules having a molecular weight of less than 1000 daltons, can be present).

"Recombinant nucleic acid" refers to a nucleic acid in a form not normally found in nature. That is, a recombinant nucleic acid is flanked by a nucleotide sequence not naturally flanking the nucleic acid or has a sequence not normally found in nature. Recombinant nucleic acids can be originally formed in vitro by the manipulation of nucleic acid by restriction endonucleases, or alternatively using such techniques as polymerase chain reaction. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention.

"Recombinant polypeptide" refers to a polypeptide expressed from a recombinant nucleic acid, or a polypeptide that is chemically synthesized in vitro.

"Recombinant variant" refers to any polypeptide differing from naturally occurring polypeptides by amino acid insertions, deletions, and substitutions, created using recombinant DNA techniques. Guidance in determining which amino acid residues may be replaced, added, or deleted without abolishing activities of interest, such as enzymatic or binding activities, may be found by comparing the sequence of the particular polypeptide with that of homologous peptides and minimizing the number of amino acid sequence changes made in regions of high homology.

Preferably, amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

"Insertions" or "deletions" are typically in the range of about 1 to 5 amino acids. The variation allowed may be experimentally determined by systematically making insertions, deletions, or substitutions of amino acids in a polypeptide molecule using recombinant DNA techniques and assaying the resulting recombinant variants for activity.

Alternatively, where alteration of function is desired, insertions, deletions or non-conservative alterations can be engineered to produce altered polypeptides. Such alterations can, for example, alter one or more of the biological functions or biochemical characteristics of the polypeptides of the invention. For example, such alterations may change polypeptide characteristics such as ligand-binding affinities, interchain affinities, or degradation/turnover rate. Further, such alterations can be selected so as to generate polypeptides that are better suited for expression, scale up and the like in the host cells chosen for expression. For example, cysteine residues can be deleted or substituted with another amino acid residue in order to eliminate disulfide bridges.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate.

"Repertoire" or "library" refers to a library of genes encoding antibodies or antibody fragments such as Fab, scFv, Fd, LC, $V_H$, or $V_L$, or a subfragment of a variable region, e.g., an exchange cassette, that is obtained from a natural ensemble, or "repertoire", of antibody genes present, e.g., in human donors, and obtained primarily from the cells of peripheral blood and spleen. In some embodiments, the human donors are "non-immune", i.e., not presenting with symptoms of infection. In the current invention, a library or repertoire often comprises members that are exchange cassette of a given portion of a V region.

"Synthetic antibody library" refers to a library of genes encoding one or more antibodies or antibody fragments such as Fab, scFv, Fd, LC, $V_H$, or $V_L$, or a subfragment of a variable region, e.g., an exchange cassette, in which one or more of the complementarity-determining regions (CDR) has been partially or fully altered, e.g., by oligonucleotide-directed mutagenesis. "Randomized" means that part or all of the sequence encoding the CDR has been replaced by sequence randomly encoding all twenty amino acids or some subset of the amino acids.

"Target" may be used to refer to the molecule to which a reference antibody binds, "reference antibody" being an antibody for which the practitioner wants to obtain a variant with "improved" characteristics. Thus, "target" may herein be used synonymously with "antigen".

"Vector" refers to a plasmid or phage or virus or vector, for expressing a polypeptide from a DNA (RNA) sequence. The vector can comprise a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate translation initiation and termination sequences. Structural units intended for use in yeast or eukaryotic expression systems may include a leader sequence enabling extra-cellular secretion of translated protein by a host cell.
Introduction The present invention provides methods for generating engineered antibodies with the specificity of a reference antibody by replacement of portions of the $V_H$ and $V_L$ sequences of the reference antibody with sequences from human antibody repertoires. The invention also provides novel compositions comprising hybrid immunoglobulin variable domains containing a combination of frameworks and CDRs ("cassettes") from different antibody clones.

The reference antibody can be a human antibody of sub-optimal affinity, in which case the methods of the invention can be used to increase affinity or to further reduce potential for immunogenicity. Alternatively, the reference antibody may be a non-human antibody, e.g., a murine antibody, and the methods of the invention are used to derive a human or humanized antibody with the specificity of the non-human antibody. The antibodies of the present invention are rapidly isolated from libraries of antibody sequences, retain the affinity of the reference antibody, and have a high degree of homology to human antibody V-regions. Often, an antibody of the invention retains a CDR3, or the MEBSD of a CDR3, from the reference antibody. In some embodiments the antibody may comprises a CDR3 pair (i.e., the $V_H$ CDR3 and the $V_L$ CDR3), from the reference antibody.

V-Gene Cassette Libraries

The V-gene segment of both the heavy and light chain can be regarded as being comprised of a number of cassettes formed by framework and CDR segments. Thus, the $V_H$ and $V_L$-gene segments are each comprised of 5 "minimal cassettes" (CDR1, CDR2, FR1, FR2, and FR3). In the current invention, the V-regions are considered to be composed of "exchange cassettes" comprised of two or more minimal cassettes, where the exchange cassette includes at least one CDR and at least one FR joined in natural order. Thus, for example, an exchange cassette relating to CDR1 may consist of FR1-CDR1 or FR1-CDR1-FR2. There are nine such exchange cassettes in each V-gene segment, consisting of at least one framework and one CDR (and less than three frameworks) in the appropriate order.

The complete V-region includes two additional minimal cassettes, CDR3 and FR4, which are formed by somatic rearrangement and mutagenesis of additional distinct germline gene segments (the D-segment in $V_H$ and a J-segment in both $V_H$ and $V_L$). CDR3-related exchange cassettes include CDR3-FR4 or FR3-CDR-3-FR4. Hence the complete V-region has a total of twenty exchange cassettes of one to three frameworks and one to three CDRs.

In some embodiments, extended cassettes are employed in the replacement methods of the invention. These extended cassettes have at least one CDR and two frameworks that occur together naturally, i.e., are encoded by the same gene. Extended cassette include FR1-CDR1-FR2, FR2-CDR2-FR3, and in those embodiments that involve exchange of CDR3 sequences, FR3-CDR3-FR4.

Repertoires of novel antibody V-regions can be constructed by recombinant DNA techniques comprising a plurality of sequences encoding one or more exchange cassettes and one or more cloned segments from a reference antibody. Such repertoires encode hybrid V-regions which do not exist naturally and which contain recombined sequences from different antibody V-genes.

The methods comprising replacing an exchange cassette of a variable region with a corresponding exchange cassette from an antibody that is encoded by a different gene can be performed sequentially or concurrently. Thus, a reference antibody in which one exchange cassette has been replaced by a corresponding library of sequences from other antibody genes can be selected for antigen binding at the same time that a different exchange cassette is replaced by a separate library of corresponding exchange cassette sequences and selected for antigen binding. Alternatively, one selection step can be performed after the other.

Libraries are generated using cloned cassettes of reference antibody sequences and repertoires of human immunoglobulin-derived sequences. The human repertoires can be generated by PCR amplification using primers appropriate for the desired segments from cDNA obtained from peripheral blood or spleen, in which case the repertoires are expected to contain clones with somatic mutations. Alternatively, the repertoires can be obtained by amplification of genomic DNA from non-immune system cells in order to obtain non-mutated, germline-encoded sequences.

The cassette libraries can be expressed in a variety of expression vectors and displayed on the surface of viruses, cells, or spores. Examples of display systems include yeast, bacteria or phage. In this case, host cells or phage are selected on target antigen in order to isolate clones expressing antigen-binding antibodies.

Alternatively, the cassette libraries can be expressed as soluble antibodies or antibody fragments and secreted from host cells. For example, the libraries can be expressed by secretion from *E. coli* or yeast and colonies of cells expressing antigen-binders are revealed by a colony-lift binding assay. Any suitable host cell can be used. Such cells include both prokarnotic and eukaryotic cells, e.g., bacteria, yeast, or mammalian cells.

Antibody Engineering Using Cassette Libraries

In one aspect, the invention provides methods of engineering antibodies, e.g., humanizing an antibody, involving replacement of portions of the variable region of a heavy or light chain of a reference antibody with the corresponding sequence from a repertoire of variable region sequences. For example, a humanized antibody can be generated by:

Constructing a repertoire of antibody V-gene segments (Repertoire A). Repertoire A is a library of human antibody sequences in which each member of the library is fused to a sequence encoding an exchange cassette from a reference antibody at the appropriate position such that a complete V-gene segment is generated.

Fusing the antibody V-gene segments of repertoire A to CDR3 sequences from a reference antibody and sequences encoding a FR4 and insertion into an expression vector such that a repertoire of functional V-regions can be generated (Repertoire B).

Pairing the Repertoire B with a cloned complementary V-region or a repertoire of complementary V-regions to form Repertoire C comprising functional $V_H$-$V_L$ dimers capable of binding antigen.

Expressing Repertoire C in a host cell such that $V_H$-$V_L$ dimers are secreted from the host cell or are displayed as fusion proteins on the cell surface.

Contacting the VH-VL dimers of Repertoire C with antigen and isolating clones expressing VH-VL dimers which bind antigen.

Identifying a humanized antibody V-region or repertoire of V-regions capable of binding antigen from step 5 such that each of the frameworks and one or more CDRs is derived from a human repertoire (Repertoire D).

The process may be repeated such that alternative cassettes from the reference antibody are replaced with human sequences. The process may also be carried out iteratively such that the exchange cassettes are serially replaced such that all or a large proportion of the V-gene segment of the reference antibody is replaced by human sequences.

In one embodiment, Repertoire A consists of hybrid $V_H$ gene sequences containing a functional cassette from a reference antibody and a plurality of human sequences to generate the complete $V_H$ domain. In this case, the complementary V-region is a $V_L$ region.

In an alternative embodiment, Repertoire A consists of hybrid $V_L$ sequences and the complementary V-domain is a $V_H$ domain.

The $V_H$-$V_L$ dimers may consist of functional Fv fragments or they may consist of longer antibody fragments such as Fab, Fab', $F(ab')_2$, scFv or whole immunoglobulins. The $V_H$-$V_L$ dimers may also be expressed as fusion proteins, for example on the surface of a filamentous bacteriophage. Preferably the $V_H$-$V_L$ dimers are expressed and secreted from a host cell and bind to antigen in soluble form. For example Fab or Fab' molecules can be expressed and secreted from a host cell such as *E. coli* or yeast.

The hybrid V-gene segment consists of an exchange cassette from a reference antibody and additional human sequences provided from a repertoire of human sequences to complete the V-gene segment. Preferably the reference antibody is a non-human antibody such as a rodent antibody, but the reference antibody may also itself be a human antibody. The exchange cassette has at least one framework and one CDR linked in a natural order and has no more than two frameworks and two CDRs. Examples of exchange cassettes that are often used include:

FR1-CDR1
FR1-CDR1-FR2
FR2-CDR2-FR3
CDR2-FR3, or
FR3-CDR3.

In some embodiments, a CDR in an exchange cassette is a hybrid CDR. A "hybrid CDR" in the context of this invention refers to a CDR that comprises an MEBSD from a reference antibody and additional sequence in the CDR that is different from the CDR sequence of the reference antibody. The position of MEBSD sequence can be empirically determined by one or more methods including but not limited to alanine scanning, X-ray crystallography, random point mutagenesis, etc., which are described in greater detail below. The MEBSD sub-sequence can be at any position within the CDR and typically comprises one to several amino acids. A CDR cassette can be constructed using any of the six CDRs contained within $V_H$ and $V_L$.

In order to create a repertoire library that contains the CDR MEBSD, a primer is designed with nucleotides that both code for the MEBSD and that anneal to germ-line sequences from a different region of the CDR such that some portion of the final CDR cassette includes sequence diversity represented in the human Ig repertoire. One or both framework regions that naturally adjoin the cassette CDR are included in the repertoire created. The CDR-FR cassette repertoire is then combined with the complementary sequences necessary to create a complete V-region. The complementary sequences can be derived from the reference antibody sequence or other exchange cassettes that are known to support antigen binding. The CDR-FR cassette is inserted into an expression vector along with the complementary $V_H$ or $V_L$ chain.

Combining Hybrid V-Gene Segments with CDR3 Sequences

Each hybrid V-gene segment is typically combined with CDR3 sequences from the corresponding chain of a reference antibody and a suitable FR4 segment to allow assembly of complete V-domains. The FR4 may be from the reference antibody, or may be from a cloned human J-segment gene, or a repertoire of FR4 sequences. Alternatively, a MEBSD of a CDR3 may be provided from the reference antibody and a complete human J-segment may be used to provide part of CDR3 in addition to FR4.

The MEBSD is the region within a CDR3 sequence or a pair of CDR3s required to retain the binding specificity of the reference antibody when combined with human sequences that re-constitute the remainder of CDR3 and the rest of the V-region. The MEBSD can be defined empirically or can be predicted from structural considerations.

For empirical determination, methods such as alanine scanning mutagenesis can be performed on the CDR3 region of a reference antibody (Wells, *Proc. Natl Acad. Sci. USA* 93:1-6, 1996) in order to identify residues that play a role in binding to antigen. Additional analyses can include Comprehensive Scanning Mutagenesis, in which each residue of CDR3 is replaced, one-at-a-time, with each of the 19 alternative amino acids, rather than just replacement with alanine. Binding assays, e.g., colony-lift binding assays, can be used to screen libraries of such mutants to determine those mutants that retain binding specificity. Colonies that secrete antibody fragments with assay signals reduced by at least ten-fold relative to the reference antibody can be sequenced and the DNA sequences used to generate a database of amino acid positions in CDR3 that are important for retention of binding. The MEBSD can then be defined as the set of residues that do not tolerate single-site substitution, or which tolerate only conservative amino acid substitution.

The MEBSD can also be deduced from structural considerations. For example, if the x-ray crystal structure is known, or if a model of the interaction of antibody and antigen is available, the MEBSD may be defined from the amino acids required to form suitable contact with the epitope and to retain the structure of the antigen-binding surface.

Alternatively, the MEBSD may be predicted from the primary structure of the CDR3. In $V_H$ domains, for instance, the MEBSD may, in some antibodies, correspond to a D-segment (including any deletions or identifiable N-additions resulting from the rearrangement and maturation of the reference antibody). In this case, the J-segment may be replaced by a cloned human J-segment or a repertoire of J-segments. The binding specificity of the modified reference $V_H$-domain with substituted J-segment may be determined in combination with a suitable complementary light-chain. This complementary chain can be the light chain of the reference antibody or can be a human light chain containing the CDR3 of the light chain of the reference antibody. Binding specificity can be determined by colony-lift binding assay or by another known assay methodology. If colonies secreting antigen-binding antibodies are not identified by this approach, additional sequences from the reference antibody CDR3 may be substituted for corresponding sequences in the J-segment and these additional mutants screened with the complementary light chain until a MEBSD is identified.

MEBSDs can similarly be identified in CDR3 of the light chain, in which case the complementary chain used in the screening assay comprises a VH-domain. In this case the $V_H$ domain may be derived from the reference antibody or may be a human $V_H$ domain with the CDR3 from the reference antibody. As there is no D-segment in the light chain, the MEBSD can be deduced by scanning mutagenesis or by inspection of the sequence of CDR3 and substitution of those sequences in CDR3 encoded by the V-gene segment, or those sequences encoded by the J-segment. Screening for antigen binding. e.g., by colony-lift binding assay, can be used to define which segment of the CDR3 constitutes the MEBSD.

Further, software programs such as JOINSOLVER™ Souto-Carneiro, et al., *J. Immunol.* 172:6790-6802, 2004), can be used to analyze CDR3 of immunoglobulin gene to search for D germline sequences. The strategy of JOINSOLVER® is to search for D germline sequences flanking $V_H$ and $J_H$ germline genes. Additionally, it searches for P- and N-type additions in the $V_H$D and $DJ_H$ junctions. The human D germline gene database employed includes all D segments from the IMGT databank as well as the reverse and DIR germline genes.

Thus, for example, a hybrid $V_H$ domain of the invention may be comprised of an exchange cassette from a reference antibody such as a mouse antibody, remaining V-gene sequences from a human repertoire, a D-segment from the reference antibody and a human JH-segment. In a second example, the hybrid $V_H$ or V domain may be comprised of an exchange cassette from a rodent reference antibody, remaining V-gene sequences from a human repertoire, a CDR3 region from the reference antibody and a human FR-4 segment.

In another embodiment, the hybrid V-gene segment may be comprised of entirely human exchange cassettes from two or more different human $V_H$ or $V_L$ genes. Thus, for example, one exchange cassette may be obtained from one human $V_H$-gene and may be fused to a second exchange cassette from a different human $V_H$-gene of the same or a different sub-class. Often, both functional cassettes are germ-line in sequence or have sequences close to germ-line.

The serial replacement to identify functional human V-gene cassettes compatible with antigen binding, permits rapid replacement of the V-gene segment of a reference antibody with fully human sequences. The ability to recombine exchange cassettes from two or more different antibody genes increases the potential diversity of sequences generated from the human V-gene libraries. By this approach, it is possible to recombine two or more germ-line cassettes to generate additional sequence diversity not found in the germ-line but without introducing potentially immunogenic point mutations.

Combining Selected Exchange Cassettes

In some embodiments, selection for antibodies comprising exchanged cassettes include steps where the same framework region is included in the exchange cassette for more than one selection steps, e.g., a step of replacing an FR1-CDR1-FR2 from a reference antibody is performed and a step of replacing the FR2-CDR2-FR3 from the reference antibody is also performed. In these cases, the selected antibodies are identified and then the overlapping framework region(s) (in this example, FR2) combined to created the new antibody that has the binding specificity of the reference antibody. The step of combining the overlapping framework region (i.e., FR2 in this example) can comprise combining the two independently selected framework regions in a region of high homology, or selecting one or other of the framework regions for incorporation. Combining the frameworks regions is further described in the section "Engineered antibodies". Typically, when the two framework regions are combined, they are frameworks from the same subclass. Accordingly, they have a high degree of homology (i.e., typically greater than 80% identity).

Combining of exchange cassettes can be performed by recombination between homologous regions or by fusing adjacent cassettes in natural order. Recombination can be permitted to occur by natural recombination processes in a host cell or can be performed by in vitro molecular biological techniques. For example, two homologous sequences from complementary cassettes can be digested with restriction enzymes and ligated together. Alternatively, the desired recombined sequences can be designed and generated using synthetic DNA or assembled using synthetic oligonucleotides using standard techniques well known in the art. Fusion of adjacent exchange cassettes is accomplished by standard recombinant DNA techniques for example using PCR Generation of V-Regions by Replacement of Cassettes Containing CDR3

As indicated above, the complete V-region has two additional minimal cassettes (CDR3 and FR4) not present in the V-gene segment. These additional cassettes from the reference antibody can also be substituted by sequences from a library of human antibody sequences such that a V-region is generated from entirely human sequences while retaining the antigen binding specificity of the reference antibody.

In this case, the V-gene segment is first humanized by serial replacement of functional cassettes as described above. The humanized V-gene segment is then used to guide selection of a repertoire of sequences comprising human CDR3 and FR4 sequences. A humanized or fully human antibody with at least one CDR3 containing human sequences is generated by:

Obtaining V-gene sequences from repertoire D above and combining with CDR3 sequences and FR4 sequences from a library of CDR3-FR4 sequences to form Repertoire E.

Expressing Repertoire E in a host cell and co-expressing one or a plurality of complementary chains such that a repertoire of $V_H$-$V_L$ dimers is generated.

Contacting the $V_H$-$V_L$ dimers with antigen and isolating $V_H$-VL dimers that bind antigen.

The V-gene sequences from Repertoire D may be $V_H$ sequences, in which case the complementary chain is a $V_L$ chain. Alternatively, the V-gene sequences in Repertoire D may be $V_L$ sequences and the complementary chain is a $V_H$ chain.

The library of CDR3-FR4 sequences may be entirely human in origin or may be partially comprised of human sequences with some sequences retained from the reference antibody. For example, the sequence of the J-segment-encoded region may be provided by one or a plurality of human J-segments and the remainder of the CDR3, comprised of the D-segment and any N-additions, may be from the reference antibody. Alternatively, the CDR3 may contain random sequences or synthetic sequences.

In some embodiments, the CDR3-FR4 region may be comprised by a FR3-CDR3-FR4 region. In such an embodiment, the FR3 may be, for example from a human repertoire, with a CDR3-FR4 region as described above.

Engineered Antibodies

The antibodies of the invention engineered as described herein have at least one exchange cassette from one antibody gene and a second from another antibody gene. Antibodies formed from combining two or more exchange cassettes are distinguished from naturally occurring human antibodies and other forms of engineered or in vitro or in viva selected antibodies on the basis of their sequences. The combining of two exchange cassettes generates additional combinatorial diversity not found in natural antibodies. For combinations of germ-line exchange cassettes, the origin of each cassette is readily identified from databases of human germ-line V-region sequences. For combinations involving exchange cassettes from somatically mutated antibodies, the nearest human germ-line sequence is identified by comparison of each minimal cassette in turn with the databases of V-region sequences. By this means the exchange cassettes used in the construction of a recombined V-region can be identified.

The sequences of all human germ-line V-region genes are known and can be accessed in the V-base database, provided by the MRC Centre for Protein Engineering, Cambridge, United Kingdom (Honegger & Pluckthun, *J. Mol. Biol.* 309:657, 2001; Tomlinson, et al., *J. Mol. Biol.* 227: 776, 2002; Cox, et al., *Eur. J. Immunol.* 24: 827, 1994).

The invention also provides novel human antibodies generated by recombination between exchange cassettes in one or both V-regions. Replacement of exchange cassettes provides additional diversity from recombination between different V-genes. The cassettes may be a combination of non-human and human cassettes or may be fully human.

There are 51 germ-line $V_H$ genes in humans and each of these can be recombined. There are 40 $V_{kappa}$ genes and 31 $V_{lambda}$ genes and each of the kappa or lambda genes can be recombined. Preferably the recombination is between members of the same sub-class. The $V_H$ germ-line genes are sub-divided into 7 subclasses ($V_{H1}$-$V_{H7}$) and the germ-line light chains are sub-divided into 16 sub-classes (VK1-$V_{K6}$ and $V_{lambda1}$-Vlambda10).

Recombination between functional cassettes may advantageously be performed using homologous sequences in one of the frame works. For example, the FR2 regions of antibodies within the same $V_H$-subclass are highly homologous. The FR2 region sequences of the human germline antibodies are shown below. Germline antibodies of the $V_{H2}$ sub-class have identical amino acid sequences in FR2. In the $V_{H3}$ sub-class, 9/22 germline antibody sequences have FR2 sequences identical to the consensus for this sub-class. Only 2/51 human germline antibodies differ from the consensus FR2 sequence for their particular sub-class by more than 1 amino acid out of the 14 amino acids in FR2. These are shown below in Table 1.

TABLE 1

Amino acid sequences of the Framework-2 region of human germline $V_H$ domains.

| | | | | SEQ ID NO: |
|---|---|---|---|---|
| VH1 | 1-3 | 1-02 | WVRQAPGQGLEWMG | 1 |
| | 1-3 | 1-03 | WVRQAPGQRLEWMG | 2 |
| | 1-3 | 1-08 | WVRQATGQGLEWMG | 3 |
| | 1-2 | 1-18 | WVRQAPGQGLEWMG | 1 |
| | 1-U | 1-24 | WVRQAPGKGLEWMG | 4 |
| | 1-3 | 1-45 | WVRQAPGQALEWMG | 5 |
| | 1-3 | 1-46 | WVRQAPGQGLEWMG | 1 |
| | 1-3 | 1-58 | WVRQARGQRLEWIG | 6 |
| | 1-2 | 1-69 | WVRQAPGQGLEWMG | 1 |
| | 1-2 | 1-e | WVRQAPGQGLEWMG | 1 |
| | 1-2 | 1-f | WVQQAPGKGLEWMG | 7 |
| VH2 | 3-1/ 2-1 | 2-05 | WIRQPPGKALEWLA | 8 |
| | 3-1 | 2-26 | WIRQPPGKALEWLA | 8 |
| | 3-1 | 2-70 | WIRQPPGKALEWLA | 8 |
| VH3 | 1-3 | 3-07 | WVRQAPGKGLEWVA | 9 |
| | 1-3 | 3-09 | WVRQAPGKGLEWVS | 10 |
| | 1-3 | 3-11 | WIRQAPGKGLEWVS | 11 |
| | 1-1 | 3-13 | WVRQATGKGLEWVS | 12 |
| | 1-U | 3-15 | WVRQAPGKGLEWVG | 13 |
| | 1-3 | 3-20 | WVRQAPGKGLEWVS | 10 |
| | 1-3 | 3-21 | WVRQAPGKGLEWVS | 10 |
| | 1-3 | 3-23 | WVRQAPGKGLEWVS | 10 |
| | 1-3 | 3-30 | WVRQAPGKGLEWVA | 9 |
| | 1-3 | 3-30.3 | WVRQAPGKGLEWVA | 9 |

TABLE 1-continued

Amino acid sequences of the Framework-2
region of human germline $V_H$ domains.

|  |  |  |  | SEQ ID NO: |
|---|---|---|---|---|
|  | 1-3 | 3-30.5 | WVRQAPGKGLEWVA | 9 |
|  | 1-3 | 3-33 | WVRQAPGKGLEWVA | 9 |
|  | 1-3 | 3-43 | WVRQAPGKGLEWVS | 10 |
|  | 1-3 | 3-48 | WVRQAPGKGLEWVS | 10 |
|  | 1-U | 3-49 | WFRQAPGKGLEWVG | 14 |
|  | 1-1 | 3-53 | WVRQAPGKGLEWVS | 10 |
|  | 1-3 | 3-64 | WVRQAPGKGLEYVS | 15 |
|  | 1-1 | 3-66 | WVRQAPGKGLEWVS | 10 |
|  | 1-4 | 3-72 | WVRQAPGKGLEWVG | 13 |
|  | 1-4 | 3-73 | WVRQASGYGLEWVG | 16 |
|  | 1-3 | 3-74 | WVRQAPGKGLVWVS | 17 |
|  | 1-6 | 3-d | WVRQAPGKGLEWVS | 10 |
| VH4 | 2-1/1-1 | 4-04 | WVRQPPGKGLEWIG | 18 |
|  | 2-1 | 4-28 | WIRQPPGKGLEWIG | 19 |
|  | 3-1 | 4-30.1 | WIRQHPGKGLEWIG | 20 |
|  | 3-1 | 4-30.2 | WIRQPPGKGLEWIG | 19 |
|  | 3-1 | 4-30.4 | WIRQPPGKGLEWIG | 19 |
|  | 3-1 | 4-31 | WIRQHPGKGLEWIG | 20 |
|  | 1-1 | 4-34 | WIRQPPGKGLEWIG | 19 |
|  | 3-1 | 4-39 | WIRQPPGKGLEWIG | 19 |
|  | 1-1 | 4-59 | WIRQPPGKGLEWIG | 19 |
|  | 3-1 | 4-61 | WIRQPPGKGLEWIG | 19 |
|  | 2-1 | 4-b | WIRQPPGKGLEWIG | 19 |

The sequences in the table represent only the sub-classes with more than one member.
Differences from the consensus sequence for each sub-class are underlined.

Additionally the V-gene segments may be recombined with a CDR3-FR4 cassette that can be human or that can be comprised of human and non-human sequences.

Thus, in one embodiment, a $V_H$ domain or a $V_L$ domain contains the following elements:

a V-gene segment comprised of a human exchange cassette from one human antibody gene and a second exchange cassette from a different human antibody gene a CDR3 derived at least partially from a reference antibody a FR4 sequence Often, at least one of the exchange cassettes is identical to a human germ-line sequence. The $V_H$ or $V_L$ domain in this embodiment is paired with a complementary chain to form a functional $V_H$-$V_L$ dimer, capable of binding to a defined antigen. The complementary chain typically has a CDR3 sequence derived from the same reference antibody as the first chain such that the CDR3-pair defines the specificity of antigen-binding. Most often, the second chain has a CDR3 from a reference antibody and a complete V-gene segment from a single antibody clone, such as a human germline gene.

In another embodiment, the invention provides a human $V_H$-$V_L$ dimer capable of binding to an antigen with predefined specificity comprising:

a first V-region comprised of a germline-encoded V-gene segment; a portion of CDR3 derived from a reference antibody; and additional sequences to complete the CDR3 and FR4 sequences.

a complementary V-region comprised of a V-gene segment constituted from two recombined exchange cassettes at least one of which is of germline sequence; a portion of CDR3 derived from a reference antibody; and additional sequences to complete the CDR3 and FR4 sequences.

In one example, the first V-region is a $V_H$-region and the portion of CDR3 from the reference antibody is a D-segment from a rodent antibody binding to an antigen of predefined specificity. In this case, the complementary V-region is a $V_L$-region and the portion of the CDR3 from the reference antibody can be V-gene derived or can be part of the JL-segment.

In some cases complete CDR3s from the reference antibody are used, in which case, the CDR3-pairs are sufficient to direct the binding specificity of the human $V_H$-V dimer to the same epitope as that of the reference antibody.

The recombination of two exchange cassettes from different human antibodies is used to access additional sequence diversity not found in natural human germline genes but without the need to exploit somatic mutation in order to generate antibodies of suitable affinity for the desired antigen. Such antibodies have V-gene segments comprised entirely from germline immunoglobulin sequences and are therefore expected to be minimally immunogenic in clinical use in humans. The recombination of two distinct genes can, however, introduce "junctional epitopes", i.e., sequences at the recombination site that are not found naturally and may be recognized by T-cell receptors as foreign T-cell epitopes and hence trigger an immune response. However, by appropriate choice of recombination sites, such junctional epitopes may be reduced or avoided altogether. Thus, for example, the different members of the $V_{H3}$ subclass of heavy chains are highly homologous in Framework-2 and recombination in this region can be used to avoid the generation of significant junctional T-cell epitopes.

Human V-Segment Cloning

Human V-segments corresponding to exchange cassettes can be reading obtained using techniques known in the art. For example, V-segments, both germline and affinity-matured, can be obtained from V-region repertoires from peripheral blood lymphocytes (PBL) pooled from multiple individuals using conventional cDNA cloning methods (Sambrook and Russell, eds, *Molecular Cloning: A Laboratory Manual*, 3rd Ed. vols. 1-3, Cold Spring Harbor Laboratory Press, 2001). PCR may be used to amplify desired V-segments for cloning. However, exponential amplification mechanisms are prone to random biases, and this may be compounded by the use of degenerate primers, which have variable priming efficiencies, resulting in a significant loss of diversity. Thus, when amplification is desired, it may be desirable to use a primer-independent linear amplification method, such as in vitro transcription (Sambrook and Russell, eds, *Molecular Cloning: A Laboratory Manual*, 3rd Ed, vols. 1-3. Cold Spring Harbor Laboratory Press, 2001).

In one embodiment, mRNA is isolated from human PBLs or other lymphocyte-rich tissues such as spleen using standard methods (e.g., *Current Protocols in Molecular Biology*, Ausubel, ed. John Wiley & Sons, Inc. New York, 1997).

Germ-line human V-segment sequences can be cloned from human genomic DNA by PCR or linear amplification methods in the same way that re-arranged and somatically mutated V-segment sequences are cloned from cDNA.

Screening Methods

A number of different screening procedures can be used depending on the choice of expression vector. Display screening methods are well known in the art (see. e.g., exemplary display references cited above).

In one embodiment, the antibody repertoire is expressed as Fab or Fab' fragments in *E. coli*. Such antibody fragments can be detected, for example, in a colony lift assay. The use of Fab' fragments, with an immunoglobulin hinge, permits generation of a mixture of monovalent Fab' molecules and bivalent F(ab')$_2$ fragments. The presence of F(ab')$_2$ molecules may be advantageous in the detection of antibodies to certain antigens for which the bivalent binding may contribute to avidity and thus to the intensity of the signal in the detection assay. An exemplary protocol for screening secreted molecules by a colony lift assay is briefly described below.

Vectors and methods for expression of antibody fragments from *E. coli* are known in the art (e.g., Pluckthun, Methods 2:88-96, 1991; Corisdeo and Wang, *Protein Expr Purif.* 34:270-9, 2004; Humphreys et al., *Protein Expr Purif.* 26:309-20, 2002). The heavy and light chain can be expressed from two separate promoters (such as the tac, lac or Ara promoters) or from a dicistronic message, in which case a single promoter is used. Each chain is translated. In some embodiments, a signal peptide may be presented peptide to direct secretion. Such a signal peptide may be a natural prokaryotic signal peptide such as PelB or OmpA, or may be a non-natural signal peptide (e.g., US patent application 2002/0072093).

Colony-lift binding assays for detection of binding of secreted antibody fragments to antigen coated on filters are also known (e.g., Govannoni et al., *Nucleic Acids Research* 29:e27, 2001). For library screening, the library is plated at a density of no more than ~$10^4$ per 150 mm plate or the equivalent on solid medium with antibiotic, but without transcription inducer. Thus, for a library of $10^6$, this requires at least 100 of the 150 mm plates or the equivalent. After overnight growth, the resulting colonies are lifted onto nitrocellulose filters and incubated on fresh medium for a few hours in the presence of the transcription inducer. e.g., IPTG for the lac promoter. The filter is transferred colony-side-up onto a second filter, which has been coated with antigen (0.5-20 µg/ml), blocked with non-fat dry milk, and laid onto fresh solid medium containing the inducer. The filters are incubated for a few more hours while the antibodies diffuse from the colonies to the antigen on the filter directly beneath each colony. The antigen-coated filters are then processed to detect antibodies bound to the antigen. The filters are washed and incubated for a few hours with an anti-tag antibody which binds to the epitope tag on each Fab, and which is conjugated to horse radish peroxidase (HRP). Conjugation may be direct or indirect, e.g., via biotin-streptavidin docking or the like. After washing away unbound anti-tag antibody/HRP, the filter is then incubated in the presence of the substrate (ECL Plus reagent, Amersham Biosciences) as prescribed by the vendor, and the bound Fab is detected and quantified by spectrophotometric or autoradiographic detection of the resultant chemiluminescence. As each filter is an image of the plate from which the colonies were lifted, the colonies producing antigen-binding Fabs are readily identified and recovered. Conditions for the CLBA may be optimized empirically. For example, the transcription inducer may be optimized to avoid over-expression or under-expression by experimentally determining the amount required for e.g., 100% ten-fold-over-background detection by chemiluminescence of the Fab library when a universal Fab-binder, e.g., an anti-human Ig antibody, is used as the antigen on the filter.

The stringency of selection can also be manipulated by adjusting the concentration of antigen on the filter. For example, the antigen concentration on which the Fab to be humanized produces a minimal signal, e.g., no more than 10-fold over background, may be determined and used for selection, so that Fabs with higher affinities and/or higher expression levels may be readily identified by the intensity of their signals. Expression levels may be determined in parallel by making replicate colony lifts and incubating them on filters coated with a universal Fab binder, such as an anti-human Ig antibody. The relative affinity for each colony is then determined as the ratio of its chemi-luminescent signal from the antigen filter to its signal from the Fab-binder filter, and the ratios can be compared to each other and to the same ratio for the parent non-human Fab to rank-order the selected Fabs according to affinity. Absolute affinities may then be determined by any of several methods, e.g., surface plasmon resonance methods (SPA, Fägerstam et al., 1992, *J Chromatog* 597:397-410).

Affinity Determination

Antibodies isolated from primary screens of secreted antibodies or selected from display technologies are subjected to further analysis in order to determine quantitative affinities for target antigen. Typically, the antibodies are expressed in soluble form for this purpose, which may necessitate re-formatting as a soluble fragment or as a whole IgG if the antibodies were originally isolated as fusion proteins from a surface display approach.

Affinities can be determined by a variety of competition binding studies requiring interaction of antibody in solution with native antigen, either in solution or on whole cells whole cells, and analysis of affinity from scatchard plots. Alternatively affinity may be determined on isolated antigen, for example in Enzyme-linked Immunosorbent Assays (ELISA) or by surface plasmon resonance analysis or numerous other immunoassays known in the art (see. e.g., Harlow & Lane, Using Antibodies, A Laboratory Manual, Cold Spring Harbor Laboratory Press, 1999). Harlow & Lane and similar procedure manuals also disclose techniques to map epitopes or alternatively, competition experiments, to determine whether an antibody binds to the same epitope as the donor antibody.

The first screening steps, e.g., screens that analyze replacement of one exchange cassette where the remainder of the antibody sequences are reference antibody, an antibody that has a demonstrable affinity for the antibody is selected. The affinity may be lower than the reference antibody.

Antibodies of the invention are typically high affinity antibodies and may have monovalent dissociation constants in the range 50 nM to 1 pM. Preferably the antibody has a monovalent affinity less than 10 nM and most preferably less than 1 nM.

The antibodies have affinities preferably no more than 5-fold worse than the reference antibody and most preferably have higher affinity than the reference antibody.

EXAMPLES

Construction and Screening of $V_H$ or $V_L$ Cassette Libraries

Hybrid V-regions are created by recombing part of a reference antibody with cassette libraries created from a human V-region repertoire. The process of recombination is typically done by overlap extension PCR, a procedure well known to those with skill in the art (Mehta, R K and Singh. J., *Biotechniques* 26:1082-1086, 1999). The hybrid chain can be either a $V_H$ or a $V_L$. The human V-segment repertoires can be derived from V-segments encoded by mRNA isolated from any of a number of Ig-producing B cells including those in peripheral blood or spleen. The $V_H$ or $V_L$ cassette library can be paired with the complementary chain which can be either from the reference antibody, from a human chain or from a human-reference hybrid chain, and tested for binding to the target antigen.

The exchange cassette library is typically created with two or more rounds of PCR In the first step, the sequence of the reference antibody is used to design PCR primers to the N-terminal or C-terminal regions, and a region or regions (typically the CDRs) within the V-region that will be common to all molecules in the recombined library. PCR primers are also designed to be complementary to human V-region repertoires, taking advantage of nucleotide and amino acid sequence conservation found in V-region families. The repertoire primers can be degenerate at one or more positions to account for sequence heterogeneity. The primer or primer set can be designed to amplify one or more V-region families.

Example 1. FR1-CDR1-FR2 Exchange Cassette

By way of example, three PCR reactions are used to create a hybrid V-region. The first PCR amplifies the human FR1-CDR1-FR2 region from a human V-segment repertoire using primers A and B (FIG. 1a). Primer A is selected from one or more of a set of N-terminal primers designed to amplify all germline $V_L$ regions (Welschof, M. et al., *J. Immunological Methods* 179: 203-214, 1995). Additionally, a restriction enzyme site is appended at the 5' end of Primer A for subsequent cloning into an expression vector. Primer B is one or more primers complementary to a conserved region in the middle of or at the C-terminal end of Human FR2; the region of complementarity is typically 12-15 nucleotides (nt) and can include degenerate positions to account for heterogeneity in the human germ-line.

Additionally, Primer B has a 12-15 nt region at its 5' end complementary to 12-15 nt of the reference antibody. The second PCR amplifies the CDR2-FR3-CDR3-FR4 region of the reference antibody using Primers C and D (FIG. 1b), Primers C and D having been designed using the known nucleotide sequence of the reference antibody. Typically, Primer D has a restriction site appended to its 5' end for subsequent cloning into an expression vector. The PCR reactions use standard conditions (e.g., 94° C. for 10 sec, 50° C. for 1 min and 72° C. for 30 sec, repeated for 12-25 cycles) and the resulting fragments are gel purified away from the amplification Primers A, B, C and D and the product yield is quantified. In the third and final PCR, equal molar quantities of the two PCR products are mixed and amplified with Primer A and Primer D using standard cycling conditions. The complementary regions of Primers B and C anneal and support the synthesis of a contiguous V-region that is a hybrid of the human repertoire FR1-CDR1-FR2 and the reference antibody CDR2-FR3-CDR3-FR4 (FIG. 1c). The hybrid V-region library is cloned into an expression vector using the restriction sites on Primers A and D and typically 10,000 clones are isolated for further analysis.

A specific example of the FR1-CDR1-FR2 exchange cassette is as follows. A human repertoire of FR1-CDR1-FR2 sequences was appended to the murine CDR2-FR3-CDR3-FR4 region of the anti-human cytokine antibody 19 and human FR1-CDR1-FR2 exchange cassettes that support antigen binding were selected from the repertoire. Primer A is specific for the N-termini of the human VkI V-regions; a BssHII site was appended to Primer A and used for cloning into an expression vector. Primer B is a mixture of three primers that anneal to the C-terminal end of a human FR2 repertoire. An additional 15 nt of the murine antibody 19 CDR2 sequence was added to the 5' end of Primer B as a region of annealing to Primer C in the overlap extension PCR used to construct the final V-region. Primer C anneals to the CDR2 of the murine antibody 19 $V_L$ and overlaps with the 5' end of the sequences comprising Primer B. Primer D anneals to FR4 of the murine Fab and has a SpeI site appended that is used for cloning into an expression vector.

In the first PCR. Primers A and B were used to amplify the human FR1-CDR1-FR2 exchange cassettes from first-strand cDNA of a human immune Ig repertoire derived from peripheral blood and spleen. In the second PCR, the murine 19 $V_L$ CDR2-FR3-CDR3-FR4 was amplified. Equal molar amounts of the two PCRs were mixed and amplified with Primers A and D to construct the final V-region. The library of human repertoire FR1-CDR1-FR2 exchange cassettes was thus constructed. A human germ-line Vh1-02 heavy chain containing the murine antibody 19 CDR3-FR4 was used for the complementary chain.

About 10,000 resulting recombinant antibodies were tested in a colony lift binding assay (CLBA) using the human cytokine protein as the target antigen. Two clones, FB27-A11 and FB27-A12 were selected that bound antigen. Each was a human VkI FR1-CDR1-FR2 sequence adjoined to the murine CDR2-FR3-CDR3-FR4 sequence. The FB27 clones were shown to bind human cytokine antigen in an ELISA assay.

Example 2. FR2-CDR2-FR3 Exchange Cassette

Figure 2:
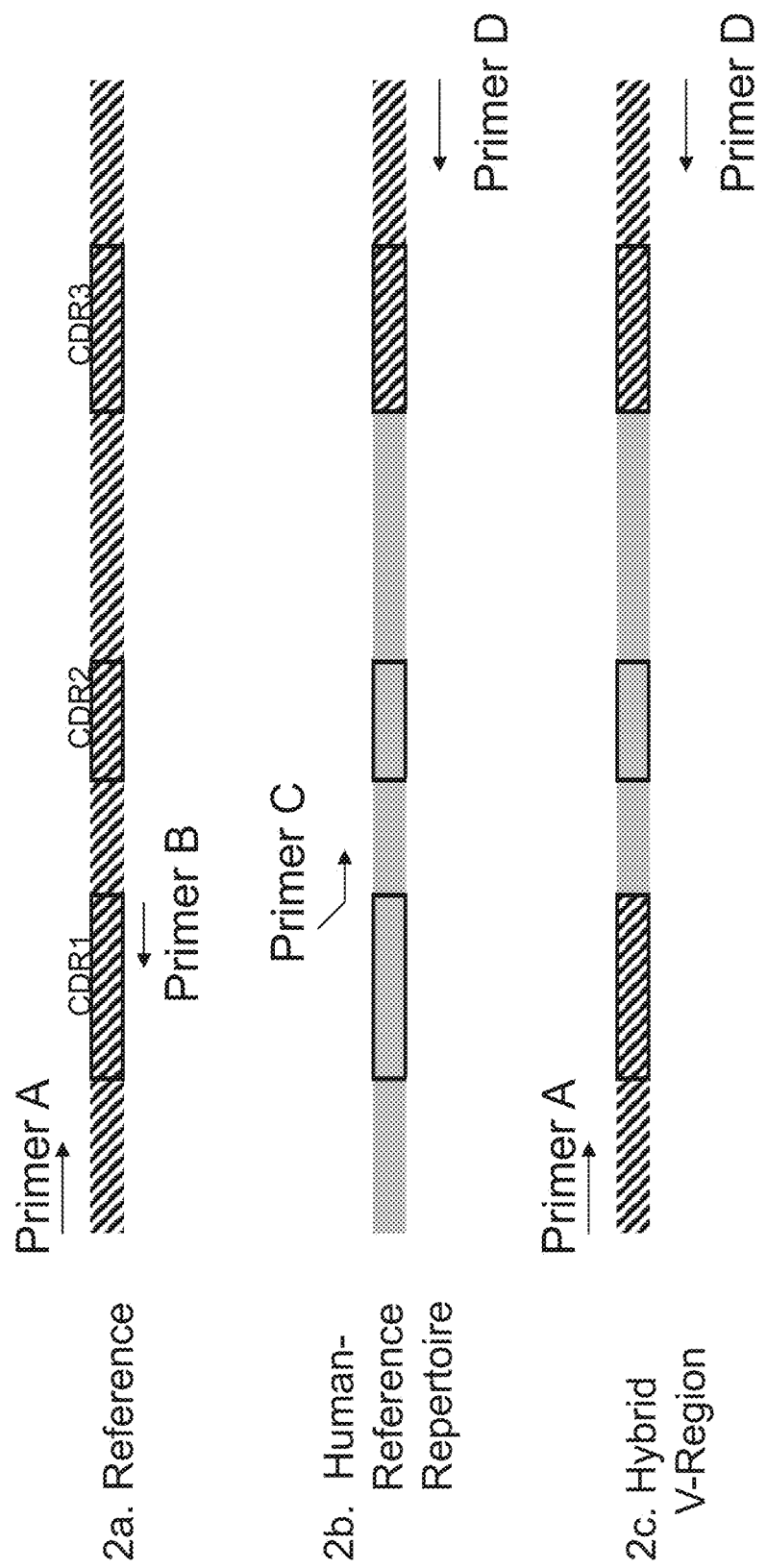
FIG. 2a-2c provides a schematic showing an exchange cassette replacement of a FR2-CDR2-FR3 cassette in a reference antibody.

In another embodiment of the invention, a human FR2-CDR2-FR3 repertoire is recombined with the FR1-CDR1 and CDR3-FR4 regions of the reference antibody. In this example, three PCR reactions are done to obtain the final hybrid V-region. The human V-region repertoire is obtained from a library of human V-segments to which the CDR3-FR4 region of the reference antibody has been appended by standard recombinant DNA procedures. Primer A and Primer B (FIG. 2a) are designed to be complementary to the N-terminus of the V-region and the C-terminal region of CDR1 of the reference antibody; typically a restriction site is appended to the 5' end of Primer A for subsequent cloning into an expression vector. For the first PCR reaction, Primers A and B are used to amplify the FR1-CDR1 region of the reference antibody using standard cycling conditions for the PCR. The resulting PCR product is gel purified away from Primers A and B and is quantified. For the second PCR reaction. Primer C (FIG. 2b) is designed to be complementary to the FR2 regions of the V-region human Ig repertoire; some positions of Primer B might be degenerate to account for variations in the human germ-line nucleotide sequence. Additionally, a 12-18 nt sequence complementary to the final 12-18 nt of CDR1 of the reference antibody is appended to the 5' end of Primer C to facilitate overlap extension PCR. Primer D (FIG. 2b) is complementary to the 3' end of FR4; typically a restriction site is appended to the 5' end of Primer D for subsequent cloning into an expression vector. Primers C and D are used to amplify the human repertoire FR2-CDR3-FR3 plus reference CDR3-FR4 regions from the human V-region repertoire library using standard cycling conditions for the PCR. The resulting PCR product is gel purified away from Primers C and D and is quantified. In the third and final PCR, equal molar quantities of the first and second PCR products are mixed and amplified with Primer A and Primer D using standard cycling conditions. The complementary regions of Primers B and C anneal and support the synthesis of a contiguous V-region that is a hybrid of the reference V-region FR1-CDR1, the human repertoire FR2-CDR2-FR3 and the reference V-region CDR3-FR4 (FIG. 2b). The hybrid V-region library is cloned into an expression vector using the restriction sites on Primers A and D and typically 10,000 clones are isolated for further analysis.

As a specific example, a human FR2-CDR2-FR3 exchange cassette repertoire was constructed in the $V_L$ of the murine anti-cytokine antibody 19. Primer A is complementary to the N-terminal region of the murine $V_L$ and has a BssHII site appended to the 5' end for cloning into an expression vector. Primer B is complementary to the final 18 nt of the murine antibody 19 $V_L$ CDR1. Primer C anneals to the N-terminal region of the VkI FR2 human repertoire; at its 5' end there is appended an 18 nt region of complementarity to Primer B. Primer D anneals to the C-terminus of the murine 19 V-region and has an appended SpeI site that is used for cloning into an expression vector.

In the first PCR, Primers A and B are used to amplify the murine FR1-CDR1 region. In the second PCR Primers C and D are used to amplify the human FR2-CDR2-FR3 repertoire from a human V-region library, each member of the library containing the murine antibody 19 $V_L$ CDR3 and either the murine or human germ-line FR4. In the third PCR, equal molar amounts of the first two PCR reactions are amplified with Primers A and D to complete the construction of the human FR2-CDR2-FR3 exchange cassette V-region repertoire. A human germ-line Vh1-02 heavy chain containing the murine 19 CDR3-FR4 region was used for the complementary chain.

About 10,000 resulting recombinant antibodies were tested in a colony lift binding assay (CLBA) using the human cytokine protein as the target antigen. Four recombinant antibodies, FB25-6-1, FB25-D3, FB25-E1 and FB26-E9 that bound the target antigen were recovered and purified. Two of the clones were human VkI FR2-CDR2-FR3 sequence adjoined to the murine FR1-CDR1 and CDR3-FR4 sequences. The other two clones were human VkIII FR2-CDR2-FR3 sequence adjoined to the murine FR1-CDR1 and CDR3-FR4 sequences. The VkIII FR2-CDR2-FR3 exchange cassettes were likely included in the library because Primer C cross-hybridized to human VkIII V-segment sequences. The FB25 and FB26 clones were shown to bind human cytokine antigen in an ELISA assay.

Example 3. FR3-CDR3-FR4 Library

The FR3-CDR3-FR4 library can be from either $V_H$ or $V_L$ and is constructed in the following way. First strand cDNA is prepared using standard procedures from mRNA derived from cells expressing an immune repertoire, for example, B cells from peripheral blood or spleen. A V-segment cDNA library containing the region from FR1 through FR3 is prepared from the first-strand cDNA by PCR. The cDNA is amplified via PCR using a forward primer(s) at the N-terminal region of FR1 and a reverse primer(s) from the C-terminal region of FR3. The PCR primers are designed to be complementary to human V-segment repertoires, taking advantage of nucleotide and amino acid sequence conservation found in V-segment families. The repertoire primers can be degenerate at one or more positions to account for sequence heterogeneity. The primer or primer set can be designed to amplify one or more V-segment families.

A V-region library containing the reference CDR3 and a FR4 is constructed first. The CDR3-FR4 region of the reference antibody is attached to the V-segment repertoire by one of several methods that include ligation via a compatible restriction site or overlap extension PCR. The FR4 region can be the same as the reference antibody or it can be converted to human germ-line sequence at those residues in which the reference and human germ-line J regions differ.

Figure 3:
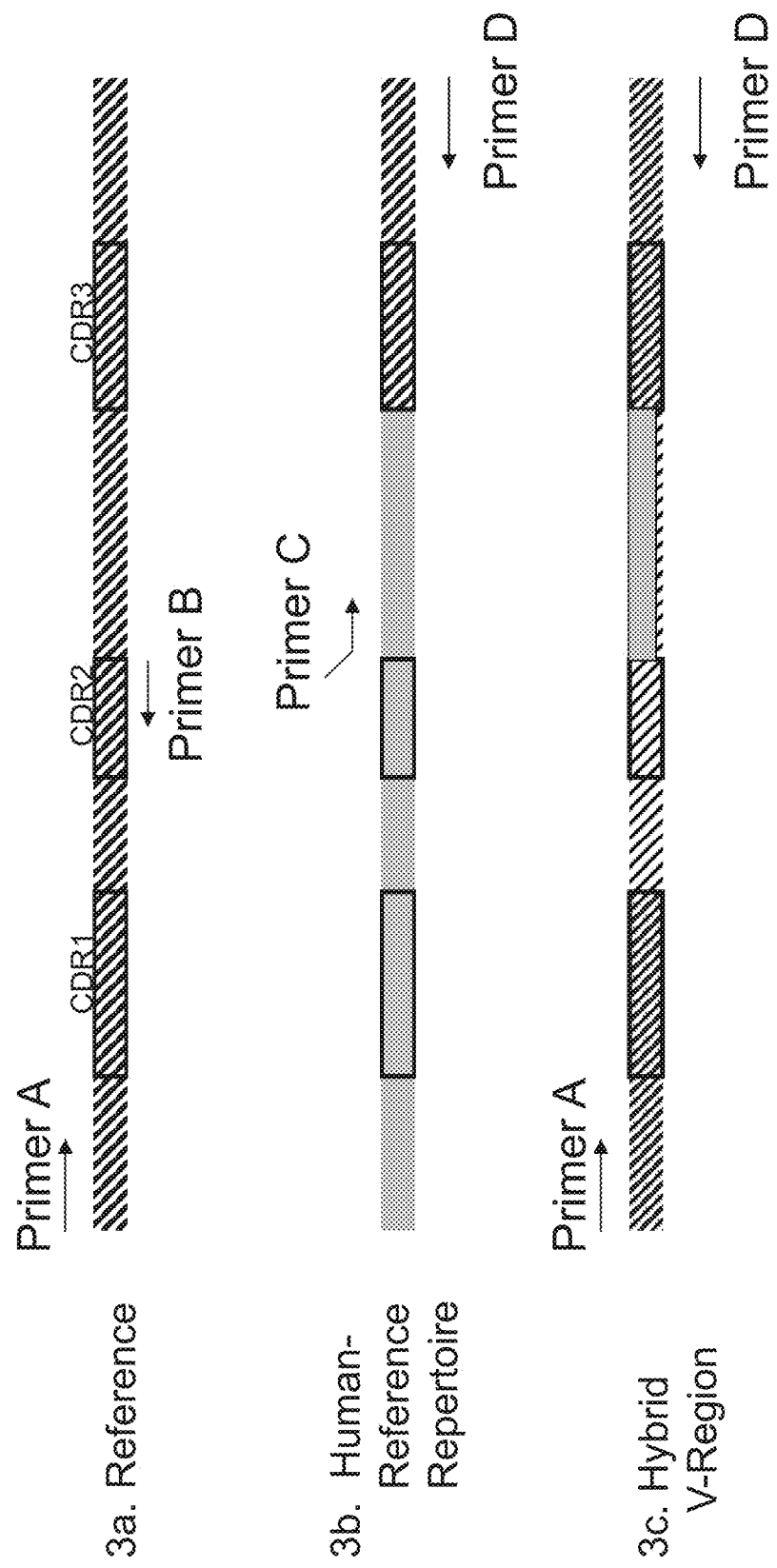
FIG. 3a-3c provides a schematic showing replacement of a FR3-CDR3-FR4 in a reference antibody.

The FR3-CDR3-FR4 repertoire is constructed with three PCR reactions as follows. In the first PCR (FIG. 3a), Primer A and Primer B are used to amplify the FR1-CDR1-FR2-CDR2 region of the reference antibody. Typically, Primer A has an appended restriction site for cloning into an expression vector. In the second PCR, the FR3-CDR3-FR4 repertoire can be derived from the constructed V-region library by a first PCR using a forward Primer C to the N-terminal end of FR3 and a reverse Primer D to the C-terminal end of FR4. Typically, the PCR primers are 15-20 nt in length and the forward Primer C has a 12-15 nt region of the reference CDR2 at its 5' end used for overlap extension PCR. Primer C may contain one or more members and might be degenerate at one or more positions to reflect sequence heterogeneity in the human germ-line at these positions. Typically, Primer D has an appended restriction site for cloning into an expression vector. The PCR reactions use standard conditions (e.g., 94° C. for 10 sec, 50° C. for 1 min and 72° C. for 30 sec, repeated for 12-25 cycles) and the resulting fragments are gel purified away from the amplification Primers A, B, C and D and the product yield is quantified. In the third PCR, equal molar amounts of the first two PCR reactions are amplified with Primers A and D to complete the construction of the human FR3-CDR3-FR4 repertoire. The FR3-CDR3-FR4 human Ig repertoire is diverse in FR3 and common in the CDR3-FR4 region. The FR3-CDR3-FR4 library is cloned into an expression vector and is co-expressed with the complementary $V_H$ or $V_L$ chain. The $V_H$ or $V_L$ chain can be derived from the reference antibody or can be an engineered human chain.

A FR3-CDR3-FR4 library was made for both the $V_H$ or $V_L$ chains of a murine reference antibody clone 10 that binds to a human cytokine protein. About 10,000 resulting recombinant antibodies for both the $V_H$ or $V_L$ chains were tested in a colony lift binding assay (CLBA) using a human cytokine protein as the target antigen. Two recombinant antibodies from the VH FR3-CDR3-FR4 library, B-17-11-H1 and B-17-15-H5, that bound the target antigen were recovered and purified. Two recombinant antibodies from the $V_L$ FR3-CDR3-FR4 library, B-18-17-H7 and B-18-20-H10, that bound the target antigen were recovered and purified. All of the $V_H$ or $V_L$ clones had a FR3 sequence similar to and sometimes identical with a human germ-line FR3 sequence. The B antibody clones for both the $V_H$ or $V_L$ chains were shown to bind human cytokine antigen in an ELISA assay.

Example 4. CDR3-FR4 Replacement

Figure 4:
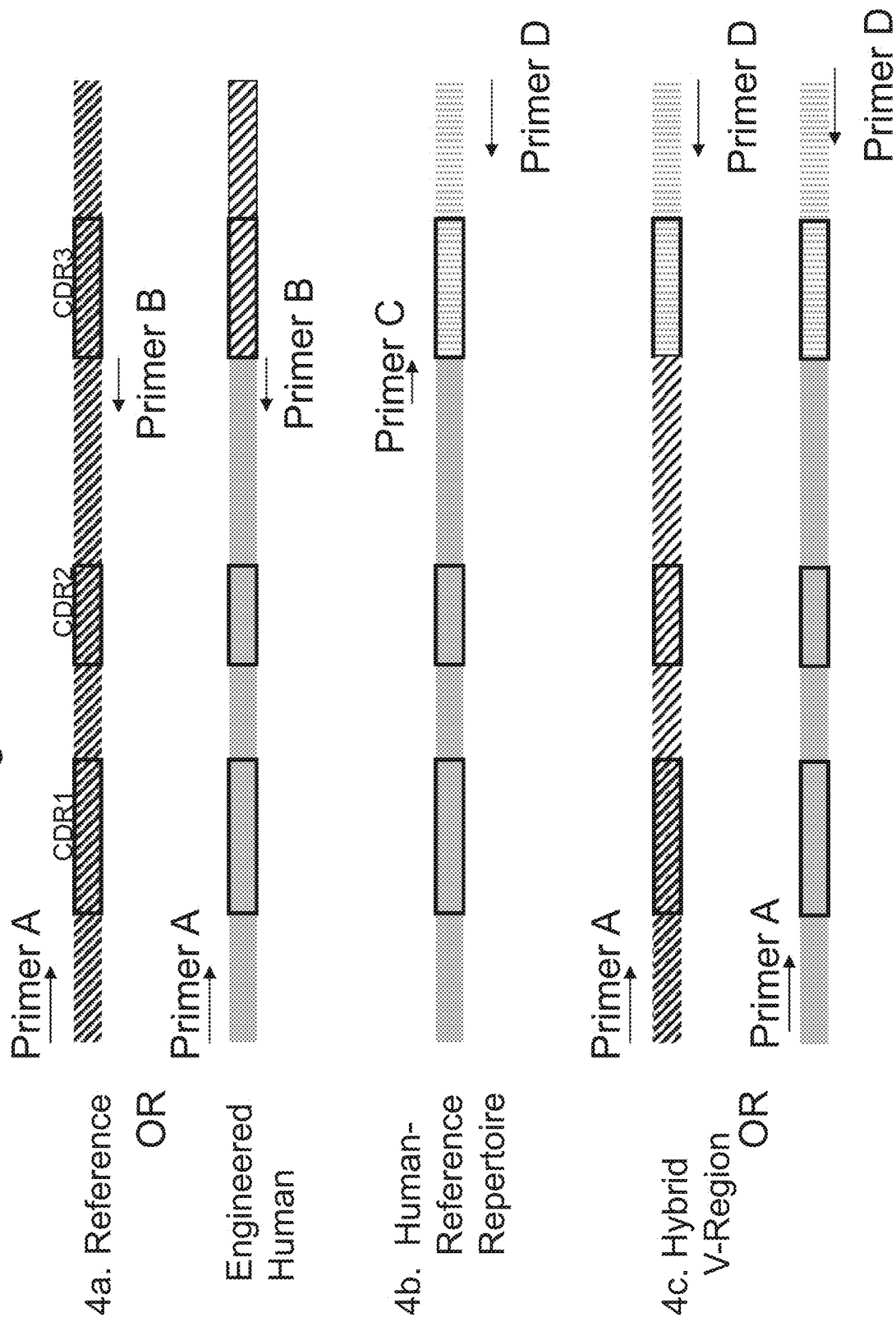
FIG. 4a-4c provides a schematic showing replacement of a CDR3-FR4 region of a reference antibody.
Figure 5:
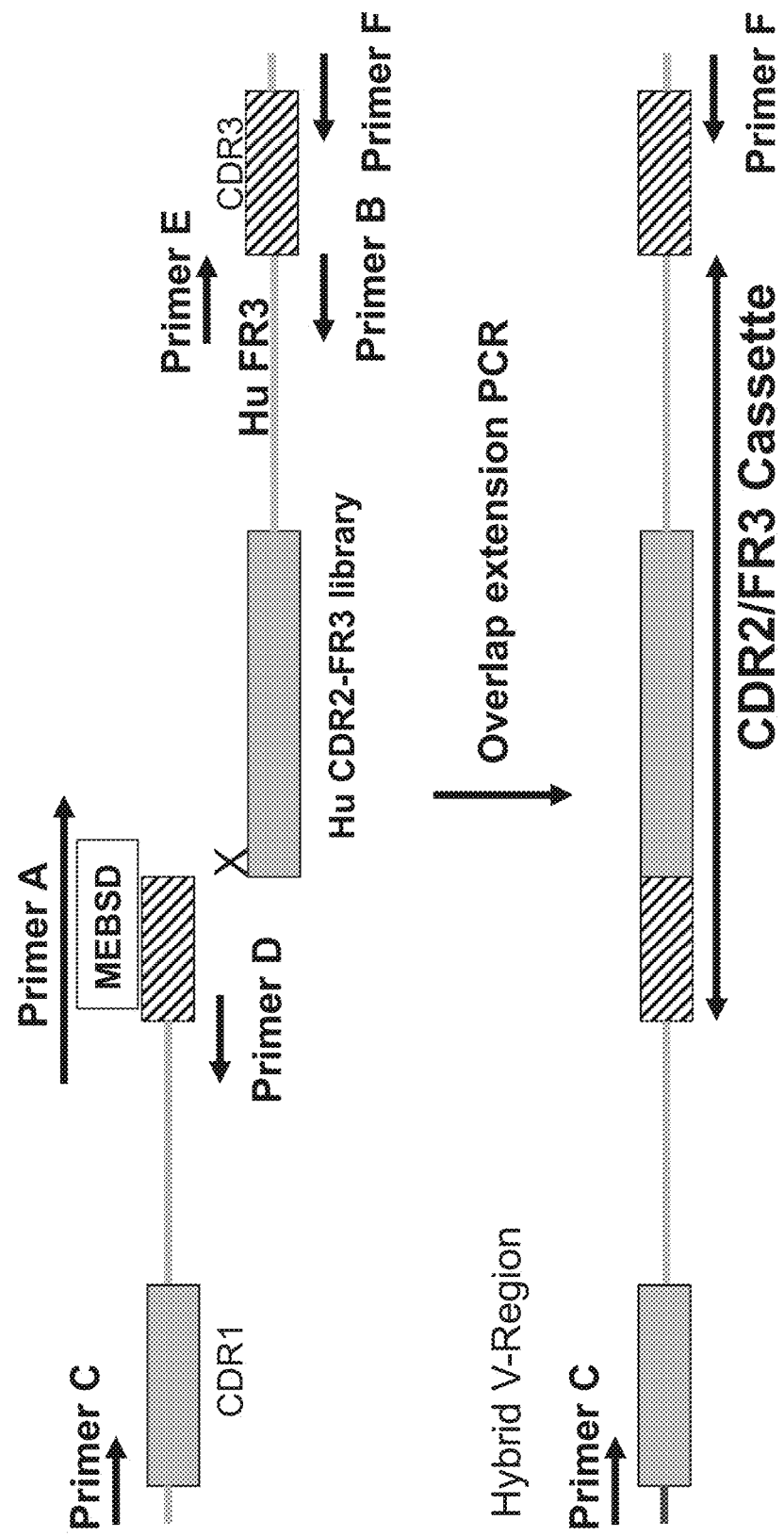
FIG. 5 provides a schematic showing an exchange cassette replacement of a CDR2-FR3 cassette in a reference antibody, where the CDR2 of the reference antibody retains the minimal essential binding specificity determinant.

The CDR3-FR4 region of the reference antibody can be replaced by a CDR3-FR4 exchange cassette selected from a human repertoire. A CDR3-FR4 library can be fused to one or a pool of V-segments derived from V-regions that are known to bind the reference antigen. In the first PCR, Primers A and B (FIG. 4a) are used to amplify a V-segment either from the reference antibody or from a engineered human V-segment that is known to bind the target antigen. In FIG. 4a, Primer A anneals to N-terminus of the V-region and typically has a restriction site appended to the 5' end for cloning into an expression vector. Primer B anneals to the C-terminal end of FR3 and has a restriction site appended to it for attaching the PCR product to the CDR3-FR4 exchange cassette repertoire. In the second PCR, Primers C and D (FIG. 4b) are used to amplify the CDR3-FR4 exchange cassette from a human Ig repertoire mRNA derived from peripheral blood lymphocytes and/or spleen lymphocytes. Primer C anneals to FR3 or to FR3 and a portion of CDR3. Primer C also contains a restriction site that can be used to fuse the CDR3-FR4 exchange cassette library to the V-segment(s). Primer D contains one or more sequences that anneal to the C-terminal ends of human V-regions; Primer D may contain a degenerate nucleotide mix at one or more positions that reflects the sequence diversity in the human J-region repertoire. Additionally, Primer D contains a restriction site that can be used for insertion of the resulting V-regions into an expression vector.

By way of specific example, the murine $V_L$ CDR3-FR4 region of a engineered human anti-cytokine antibody 19 was replaced with a human CDR3-FR4 exchange cassette. Primer A binds to the N-terminal regions of FB39-3, FB38-4, FB44-15 and FB44-16, a pool engineered human $V_L$ chains each of which binds to human cytokine when paired with a complementary $V_H$. Primer A contains the BssHII restriction site used for cloning into an expression vector. Primer B anneals to the C-terminal ends of FR3 for each $V_L$ of the pool of FB39-3, FB38-4, FB44-15 and FB44-16. Primer B contains the Bst1107I restriction site to facilitate ligation of the V-segments to the CDR3-FR4 exchange cassette library. Primer C anneals to human FR3 of the VkIII $V_L$ family. Primer D contains three primers that anneal to the FR4 sequences for the human Jk1, Jk2, Jk3, Jk4 and Jk5 J-regions. Primer D contains a SpeI site used to clone the V-regions into an expression vector.

In the first PCR, Primers A and B are used to amplify the V-segments from a pool of four engineered human $V_L$ chains that contain the murine reference antibody 19 CDR3-FR4. The $V_L$ chains are known to bind to human cytokine antigen when paired with a complementary human germ-line Vh1-02 heavy chain with the reference $V_H$ CDR3 and an engineered human FR4 attached. In the second PCR, Primers C and D are used to amplify a CDR3-FR4 exchange cassette repertoire from human spleen first-strand cDNA. The PCR products from the first and second reactions are digested with Bst1107I, gel purified and ligated together using standard procedures. The resulting ligation products are digested with BssHII and SpeI and inserted into an expression vector. A V-segment containing a human germ-line Vh1-02 heavy chain, the murine 19 CDR3 and a human germ-line FR4 was used for the complementary chain.

About 10,000 resulting recombinant antibodies were tested in a colony lift binding assay (CLBA) using the human cytokine protein as the target antigen. One recombinant antibody, FB67-2, that bound the target antigen were recovered and purified. The CDR3-FR4 exchange cassette was a different amino acid sequence from the reference CDR3-FR4 and appeared to be derived from the VkIII subclass of human VL. The FB67-2 clone was shown to bind human cytokine antigen in an ELISA assay.

Please replace the heading preceding paragraph 157 with the following heading:

Example 5. CDR2-FR3 Cassette

The preceding examples describe exchange cassettes containing complete CDR regions and at least one adjoining framework. Alternatively, a CDR cassette can be comprised of a sub-sequence of the CDR that is derived from the reference antibody along with a repertoire library containing the remainder of the CDR region.

By way of a specific example, a cassette library was made for the $V_H$ CDR2-FR3 region of a murine reference antibody, clone 10, that binds a human cytokine. The clone 10 Vh CDR2 is 17 amino acids in length and its amino acid sequence most similar to the human Vh3 subclass. The MEBSD was defined empirically using point mutagenesis. All of the alterations in positions 1-6 of the reference CDR2 resulted in a complete loss of binding activity whereas amino acid substitutions at positions 7-17 did not abolish antigen binding.

The V-regions containing the CDR cassette library are constructed with five PCR reactions as shown in FIG. 5. The PCR reactions use standard conditions (e.g., 94° C. for 10 sec, 50° C. for 1 min and 72° C. for 30 sec, repeated for 12-25 cycles) and the resulting fragments are gel purified away from the amplification primers and the product yield is quantified. The first PCR reaction is done with Primers A and B. Primer A contains the nucleotide sequence that encodes the MEBSD along with 13 downstream nucleotides that anneal to most germ-line CDR2 sequences of the human Vh3 family. Primer B anneals to the C-terminal end of FR3 and is designed to capture the human germ-line sequences of the Vh3 repertoire. Primers A and B are used to amplify the human Ig repertoire from spleen first strand cDNA resulting in a CDR2-FR3 exchange cassette library. In the second PCR reaction Primers C and D are used to amplify the human FR1-CDR1-FR2 from a $V_H$ chain known to bind the target antigen when paired with a complementary $V_L$. Primer C contains a restriction site used to clone the final V-region into an expression vector. Primer D contains a region of complementarity to Primer A to facilitate overlap extension PCR. In the third PCR. Primers E and F are designed to amplify the CDR3-FR4 region of either the reference $V_H$ or an engineered human $V_H$ that is known to support antigen binding when paired with the complementary $V_L$. Primer E has a region of complementarity to Primer B in order to facilitate overlap extension PCR. Primer F contains a restriction site used for cloning the V-region into an expression vector.

In the fourth PCR, equal molar amounts of the first and second PCR reactions are included in a PCR reaction along with Primers C and B. The resulting fragments are gel purified away from the amplification Primers B and C and the product yield is quantified. In the final PCR reaction, equal molar amounts of the fourth and third PCR reactions are combined and amplified with Primers C and F to construct the final V-region. The PCR products are purified and digested with the restriction enzymes that cleave the sites included in Primers C and F. The CDR2-FR3 cassette library is inserted into an expression vector along with a complementary $V_L$ chain. Typically, a library of 10,000 members is screened for binding to antigen by CLBA.

The CDR2-FR3 cassette library was screened by CLBA using the human cytokine antigen as a target. Several antibodies, including B180-27-4B, B180-32-6F, B180-33-7B and B180-34-7F, were purified that showed binding to the human cytokine protein when tested in an ELISA assay.

Example 6. Iterative Exchange Cassette Construction and Screening

The previous examples describe the construction of exchange cassette libraries that are a hybrid of human Ig repertoire library and a common sequence from the reference antibody. Exchange cassette libraries can also be constructed where the common sequence is not from the reference antibody, but rather, is from a selected human exchange cassette or from a selected engineered human V-region. Such an iterative exchange cassette strategy can be used for either the $V_H$ or the $V_L$. The iterative exchange cassette library is cloned into an expression vector and is co-expressed with the complementary $V_H$ or $V_L$ chain. The complementary $V_H$ or $V_L$ chain can be derived either from the reference antibody or from an engineered human V-region.

By way of specific example, a human Ig repertoire library of FR2-CDR2-FR3 was joined with a selected FR1-CDR1-FR2 exchange cassette; the region of joining was a common sequence within FR2. The construction was done with three PCR reactions as shown in FIG. 6. The reference antibody 19 binds a human cytokine antigen. A Vii-region was selected from a Fab (FB42-8) that showed binding to a human cytokine antigen. The $V_H$-region comprised a human V-segment joined to the reference CDR3 and a human germ-line FR4. In the first PCR (FIG. 6a), Primer A and Primer B were used to amplify the FR1-CDR1-FR2 cassette from FB42-8; Primer B annealed to the C-terminal end of FR2. Primer A contains a restriction site used for cloning into an expression plasmid. In the second PCR reaction (FIG. 6b), Primer C and Primer D were used to amplify the FR2-CDR2-FR3 region from a $V_H$-region library that contains the reference CDR3 and a human germ-line FR4. Primer C anneals to the C-terminal end of FR2 and is the complementary sequence of Primer B. Typically, Primer D has an appended restriction site for cloning into an expression vector. The PCR reactions use standard conditions (e.g., 94° C. for 10 sec, 50° C. for 1 min and 72° C. for 30 sec, repeated for 12-25 cycles) and the resulting fragments are gel purified away from the amplification Primers A, B, C and D and the product yield is quantified. In the third PCR, equal molar amounts of the first two PCR reactions are amplified with Primers A and D to complete the construction of the V-region containing the human FR2-CDR2-FR3 exchange cassette repertoire. The FR2-CDR2-FR3 exchange cassette library was cloned into an expression vector and co-expressed with four complementary engineered human $V_L$ chain(s).

About 10,000 resulting recombinant antibodies for the FR2-CDR2-FR3 exchange cassette library were tested in a colony lift binding assay (CLBA) using a human cytokine protein as the target antigen. Three Fabs (FB48-12, FB48-18 and FB48-20) were selected that showed binding to the human cytokine antigen in an ELISA assay.

Example 7. Cassette Reconstruction

The exchange cassettes described in the previous examples were hybrids of human and reference sequence. The selected human exchange cassettes can be recombined in order to create full or partial human V-regions. Typically, one or several human exchange cassettes selected from Fabs that bind target antigen are fused with overlap extension PCR or ligation to create V-regions that are tested for antigen binding. Such an exchange cassette reconstruction strategy can be used for either the $V_H$ or the $V_L$. The exchange cassettes can originate from the same or different V-region subclasses so that the final reconstructed V-region is either similar to a single human germ-line or is a hybrid similar to two or more human germ-lines. The reconstructed exchange cassette or exchange cassette library is cloned into an expression vector and is co-expressed with the complementary $V_H$ or $V_L$ chain. The complementary $V_H$ or $V_L$ chain can be derived either from the reference antibody or from a engineered human V-region.

By way of specific example, three PCR reactions can be used to recombine exchange cassettes (FIG. 7). Several $V_L$ FR1-CDR1-FR2 human exchange cassettes for reference antibody 19 that bound human cytokine antigen were identified. In the first PCR (FIG. 7a), Primer A and Primer B were used to amplify the FR1-CDR1-FR2 exchange cassette region from the V-region DNA. Typically, Primer A has an appended restriction site for cloning into an expression vector. Primer A can be one or a pool or primers that anneal to the N-terminal regions of FR1 of each exchange cassette to be amplified. Primer B can be one or a pool or primers that anneal within FR2 of each exchange cassette to be amplified. Several VL FR2-CDR3-FR3 human exchange cassettes that bound human cytokine antigen were identified. In the second PCR (FIG. 7b). Primer C and Primer D were used to amplify the FR2-CDR2-FR3 region from the V-region DNA, along with the reference CDR3 and a FR4. Typically, Primer D has an appended restriction site for cloning into an expression vector. Primer C can be one or a pool or primers that anneal within FR2 of each exchange cassette to be amplified. Typically, Primer B and Primer C are complementary sequences to facilitate the overlap extension, third PCR. The PCR reactions use standard conditions (e.g., 94° C. for 10 sec, 50° C. for 1 min and 72° C. for 30 sec, repeated for 12-25 cycles) and the resulting fragments are gel purified away from the amplification Primers A, B, C and D and the product yield is quantified. In the third PCR, equal molar amounts of the first two PCR reactions are amplified with Primers A and D to complete the construction of the human $V_L$ V-region repertoire. The $V_L$ repertoire was cloned into an expression vector and co-expressed with a complementary $V_H$ chain.

About 10,000 resulting recombinant antibodies for the V-region repertoire library were tested in colony lift binding (CLBA) and ELISA assays using a human cytokine protein as the target antigen. Three Fabs (FB30-G4, FB31-13-1 and FB40-1-H) were selected that showed binding to the human cytokine antigen in an ELISA assay.

The FR1-CDR1-FR2 and FR2-CDR2-FR3 exchange cassettes from FB30-G4 are both most similar to the human VkI subclass. The FR1-CDR1-FR2 and FR2-CDR2-FR3 exchange cassettes from FB31-13-1 are both most similar to the human VkIII subclass. The FR1-CDR1-FR2 and FR2-CDR2-FR3 exchange cassettes from FB40-1-1H are most similar to the human VkIII and human VkI subclasses, respectively.

Surface plasmon resonance analysis (BIACORE®) was used to determine the binding affinities of the engineered human Fabs derived by cassette reconstruction. For this purpose, Fab fragments were purified from culture medium of E. coli clones expressing the Fab using Protein G affinity chromatography. From the binding kinetics determined from surface plasmon resonance analysis, a cassette-reconstructed Fab was identified with the binding specificity of antibody 19 and an affinity of 20 pM, which is similar to the affinity of the antibody 19 reference antibody (10 pM).

Re-constructed Fabs with the specificity of antibody 10 were identified with affinities of 0.4 nM (compared with an affinity of 1.5 nM for clone 10), demonstrating that cassette exchange can be used to identify Fabs with a higher affinity than the corresponding reference antibody.

The above examples are provided by way of illustration only and not by way of limitation. Those of skill in the art will readily recognize a variety of noncritical parameters that could be changed or modified to yield essentially similar results.

All publications, patent applications, accession numbers, and other references cited in this specification are herein incorporated by reference as if each individual publication or patent application were specifically and individually indicated to be incorporated by reference.

What is claimed is:

1. A method of engineering an antibody that retains the binding specificity of a reference antibody for a target antigen, the method comprising:

(a) obtaining a variable region from the reference antibody;

(b) replacing at least one exchange cassette obtained from a V gene segment, FR1-CDR1-FR2-CDR2-FR3, of the variable region of the reference antibody with a library of corresponding human exchange cassettes from human V-gene segments comprised of immunoglobulin sequences that are germline or a V-gene segment having a human exchange cassette from one human antibody gene, thereby generating a library of hybrid V-regions comprising members in which the at least one exchange cassette of the variable region of the reference antibody is replaced with human corresponding exchange cassettes encoded by different genes, with the proviso that the exchange cassette has less than three framework regions, wherein the at least one exchange cassette obtained from the V-segment of the variable region of the reference antibody includes at least one intact CDR adjoined to at least one intact FR of the V-segment that are together naturally occurring;

(c) pairing the library of hybrid V regions of (b) with a complementary V-region; and (d) selecting an antibody comprising a hybrid V region having at least one human exchanged cassette as generated in step (b) that has the binding specificity of the reference antibody and has a reduced potential for immunogenicity in humans, wherein the method is repeated such that alternative exchange cassettes from the antibody comprising a hybrid V region are replaced with human V region cassette sequences as generated in step (b) or wherein the method is carried out iteratively such that the exchange cassettes are serially replaced such that all of the V-gene segment of the reference antibody is replaced by human sequences, (e) replacing a second exchange cassette of the V region of the reference antibody with a library of corresponding exchange cassettes from human V-gene segments comprised of immunoglobulin sequences that are germline or a V-gene segment having a human exchange cassette from a different human antibody gene to create a second hybrid library of hybrid V regions, comprising members in which the second exchange cassette of the variable region of the reference antibody is replaced with human corresponding exchange cassette encoded by a different gene, with the proviso that the exchange cassette has less than three framework regions;

wherein the second exchange cassette obtained from the V-segment of the variable region of the reference antibody comprises at least one intact CDR adjoined to at least one intact FR of the V-segment that are together naturally occurring;

(f) pairing the second library of hybrid V regions with a complementary V-region;

(g) selecting an antibody comprising a hybrid V region having the second human exchanged cassette as generated in step (e), which antibody has a binding affinity for the target antigen; and (h) combining the at least one human exchanged cassette of the engineered antibody of (d) with the second human exchange cassette of the antibody of (g), to obtain an antibody with the binding specificity of the reference antibody and a higher binding affinity for the target antigen than the reference antibody and having a reduced potential for immunogenicity in humans, wherein the antibody has a hybrid V-region that comprises at least two human exchanged cassettes.

2. The method of claim 1, wherein the complementary V-region has a naturally occurring V-segment.

3. The method of claim 1, wherein the complementary V-region has a germline V-segment.

4. The method of claim 1, wherein the complementary V-region is a hybrid V-region.

5. The method of claim 1, wherein the complementary V-region is a hybrid V region that is a member of a library that comprises different hybrid V-regions.

6. The method of claim 1, wherein the at least one exchange cassette is selected from the group consisting of FR1-CDR1, FR1-CDR1-FR2, FR2-CDR2-FR3, and CDR2-FR3.

7. The method of claim 1, further comprising a step of replacing a CDR3-FR4 of the hybrid V-region with a library of CDR3-FR4 regions comprised of immunoglobulin sequences that are germline, pairing the variable region with a complementary variable region, and selecting an antibody that retains the binding specificity for the target antigen and that has a higher binding affinity to the target antigen than the reference antibody.

8. The method of claim 1, further comprising: a step of replacing the FR4 of the hybrid V-region with a library of FR4 sequences, comprised of immunoglobulin sequences that are human germline.

9. The method of claim 1, wherein the complementary V-region of (f) comprises a naturally occurring V-segment.

10. The method of claim 1, wherein the complementary V-region of (f) is a hybrid V-region.

11. The method of claim 1, wherein the complementary V-region of (f) is a hybrid V region that is a member of a library that comprises different hybrid V-regions.

12. The method of claim 1, wherein the variable region is from the heavy chain of the reference antibody.

13. The method of claim 1, wherein the variable region is from the light chain of the reference antibody.

14. The method of claim 1, wherein the antibodies are expressed and secreted in soluble form from a host cell and bind to an antigen.

15. A method of engineering an antibody that retains the binding specificity of a reference antibody for a target antigen, the method comprising:

(a) obtaining a variable region of a reference antibody having a desired binding specificity;
(b) replacing the FR1-CDR1-FR2 of the variable region of the reference antibody with a library of human FR1-CDR1-FR2 regions from human V-gene segments comprised of immunoglobulin sequences that are germline to create a library of hybrid variable regions, pairing the hybrid variable regions with a complementary variable region, and selecting an antibody having a detectable affinity for the target antigen;
(c) replacing the FR2-CDR2-FR3 of the variable region of the reference antibody with a library of human FR2-CDR2-FR3 regions from human V-gene segments comprised of immunoglobulin sequences that are germline to create a library of hybrid variable regions, pairing the hybrid variable regions with a complementary variable region, and selecting an antibody having a detectable affinity for the target antigen;
(d) combining the human FR1-CDR1-FR2 of the hybrid variable region of the antibody selected in (b) with the human FR2-CDR2-FR3 of the hybrid variable region of the antibody selected in (c) to obtain an antibody with a human FR1-CDR1-FR2-CDR2-FR3 variable region V gene segment, which antibody has the binding specificity of the reference antibody and has a higher binding affinity for the target antigen than the reference antibody and has a reduced potential for immunogenicity in humans.

16. The method of claim 15, wherein (b) and (c) are performed sequentially.

17. A method of engineering an antibody that retains the binding specificity of a reference antibody for a target antigen, the method comprising:

(a) obtaining a variable region of a reference antibody having a desired binding specificity;
(b) replacing the FR1-CDR1-FR2 of the variable region of the reference antibody with a library of human FR1-CDR1-FR2 regions comprised of immunoglobulin sequences that are germline to create a library of hybrid variable regions, pairing the hybrid variable regions with a complementary variable region, and selecting an antibody having a detectable affinity for the target antigen;
(c) replacing the CDR2-FR3 of the variable region of the reference antibody with a library of human CDR2-FR3 regions comprised of immunoglobulin sequences that are germline to create a library of hybrid variable regions, pairing the hybrid variable regions with a complementary variable region, and selecting an antibody having a detectable affinity for the target antigen,
(d) combining the FR1-CDR1-FR2 of the hybrid variable region of the antibody selected in (b) with the CDR2-FR3 of the hybrid variable region of the antibody selected in (c) to obtain an antibody with a human variable region V segment, which antibody has the binding specificity of the reference antibody and a higher binding affinity for the target antigen than the reference antibody and has a reduced potential for immunogenicity in humans.

18. The method of claim 1, wherein the antibody is an Fv fragment, a Fab, a Fab', a F(ab')$_2$, or a scFv.

19. The method of claim 17, wherein the antibody is an Fv fragment, a Fab, a Fab', a F(ab')$_2$, or a scFv.

* * * * *